(12) United States Patent
Buck, Jr. et al.

(10) Patent No.: US 7,045,310 B2
(45) Date of Patent: May 16, 2006

(54) REDOX REVERSIBLE BIPYRIDYL-OSMIUM COMPLEX CONJUGATES

(75) Inventors: Harvey B. Buck, Jr., Indianapolis, IN (US); Zhi David Deng, Carmel, IN (US); Eric R. Diebold, Noblesville, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 713 days.

(21) Appl. No.: 09/999,110

(22) Filed: Nov. 1, 2001

(65) Prior Publication Data

US 2002/0090632 A1  Jul. 11, 2002

Related U.S. Application Data

(62) Division of application No. 09/322,791, filed on May 28, 1999, now Pat. No. 6,352,824.

(60) Provisional application No. 60/087,576, filed on Jun. 1, 1998.

(51) Int. Cl.
*G01N 33/53* (2006.01)
*G01N 33/72* (2006.01)

(52) U.S. Cl. ............... 435/7.93; 435/4; 435/5; 435/6; 435/7.1; 435/7.93; 436/15; 436/66; 436/67; 436/84; 436/172; 436/805; 436/806; 436/501; 436/517; 436/518; 436/536; 436/544; 436/545; 530/303; 530/304; 530/385

(58) Field of Classification Search ............ 435/4, 435/6, 7.1, 7.2, 7.92, 7.93, 287.2, 968; 436/501, 436/536, 56, 66, 67, 538, 546, 164, 172; 530/303, 304, 385

See application file for complete search history.

(56) References Cited

U.S. PATENT DOCUMENTS

| 4,293,310 A | 10/1981 | Weber |
| 4,323,536 A | 4/1982 | Columbus |
| 4,381,978 A | 5/1983 | Gratzel et al. |
| 4,478,744 A | 10/1984 | Mezei et al. |
| 4,526,661 A | 7/1985 | Steckhan et al. |
| 4,545,382 A | 10/1985 | Higgins et al. |
| 4,711,245 A | 12/1987 | Higgins et al. |
| 4,830,959 A | 5/1989 | McNeil et al. |
| 4,832,814 A | 5/1989 | Root |

(Continued)

FOREIGN PATENT DOCUMENTS

EP   0 125 139 A2   11/1984

(Continued)

OTHER PUBLICATIONS

Chidsey et al., "Micrometer-Spaced Platinum Interdigitated Array Electrode: Fabrication, Theory, and Initial Use," *Anal. Chem.*, 58, 601-677, 1986.

(Continued)

*Primary Examiner*—Christopher L. Chin
*Assistant Examiner*—Gailene R. Gabel
(74) *Attorney, Agent, or Firm*—Barnes & Thornburg LLP

(57) ABSTRACT

Novel bipyridyl-osmium complex conjugates and their use in electrochemical assays are described. The redox reversible-osmium complexes can be prepared to exhibit unique reversible redox potentials and can thus be used in combination with other electroactive redox reversible species having redox potentials differing by at least 50 millivolts in electrochemical assays designed for use of multiple electroactive species in the same cell and in the same sample without interference between the two or more redox coupled conjugate systems.

4 Claims, 13 Drawing Sheets

$C_{49}H_{56}N_{10}O_3SOs$
F.W. 1055.30

U.S. PATENT DOCUMENTS

| | | | |
|---|---|---|---|
| 4,945,045 | A | 7/1990 | Forrest et al. |
| 4,954,414 | A | 9/1990 | Adair et al. |
| 4,963,245 | A | 10/1990 | Weetall |
| 4,999,632 | A | 3/1991 | Parks |
| 5,120,420 | A | 6/1992 | Nankai et al. |
| 5,141,868 | A | 8/1992 | Shanks et al. |
| 5,192,415 | A | 3/1993 | Yoshioka et al. |
| 5,243,516 | A | 9/1993 | White |
| 5,264,103 | A | 11/1993 | Yoshioka et al. |
| 5,288,636 | A | 2/1994 | Pollmann et al. |
| 5,312,762 | A | 5/1994 | Guiseppi-Elie |
| 5,352,351 | A | 10/1994 | White et al. |
| 5,366,609 | A | 11/1994 | White et al. |
| 5,405,511 | A | 4/1995 | White et al. |
| 5,427,912 | A | 6/1995 | Brown et al. |
| 5,437,772 | A | 8/1995 | De Castro et al. |
| 5,437,999 | A | 8/1995 | Diebold et al. |
| 5,438,271 | A | 8/1995 | White et al. |
| 5,491,097 | A | 2/1996 | Ribi et al. |
| 5,575,895 | A | 11/1996 | Ikeda et al. |
| 5,589,326 | A | 12/1996 | Deng et al. |

FOREIGN PATENT DOCUMENTS

| | | |
|---|---|---|
| EP | 0 167 248 A3 | 1/1985 |
| EP | 0 150 999 A2 | 8/1985 |
| EP | 0 229 780 A2 | 1/1989 |
| EP | 0 328 380 A2 | 8/1989 |
| EP | 0 402 126 B1 | 12/1990 |
| EP | 0 142 301 B1 | 11/1991 |
| EP | 0 127 958 B1 | 3/1992 |
| WO | WO 86.02734 | 5/1986 |
| WO | WO 86/03837 | 7/1986 |
| WO | WO 86/04926 | 8/1986 |
| WO | WO 91/16630 | 10/1991 |
| WO | WO 92/14741 | 9/1992 |
| WO | WO 92/14836 | 9/1992 |
| WO | 93/25907 | 12/1993 |
| WO | 94/14066 | 6/1994 |
| WO | 97/01097 | 1/1997 |
| WO | 97/32866 | 9/1997 |
| WO | WO 97/34140 | 9/1997 |

OTHER PUBLICATIONS

Niwa et al., "Fabrication and Characteristics of Vertically Separated Interdigitated Array Electrodes," *J. Electroanal. Chem.*, 267, 291-297, 1989.

Aoki et al., "Quantitative Analysis of Reversible, diffusion-Controlled Currents of Redox Soluble Species at Interdigitated Array Electrodes Under Steady-State Conditions," *J. Electroanal. Chem.*, 256, 269-82, 1988.

Surridge et al., "Electron and Counterion Diffusion Constants in Mixed-Valent Polymeric Osmium Bipyridine Films," *J. Phys. Chem.*, 98, 917-923, 1994.

Forster et al., "Synthesis, Characterization, and Properties of a Series of Osmium- and Ruthenium-Containing Metallopolymers," *Macromolecules*, 23, 4372-4377, 1990.

Zakeeruddin et al., "Towards Mediator Design: Characterization of Tris-(4,4'-Substituted-2,2'-Bipyridine) Complexes of Iron (II), Ruthenium (II) and Osmium (II) as Mediators for Glucose Oxidase of *Aspergillus niger* and other Redox Proteins," *J. Electroanal. Chem.*, 337, 253-283, 1992.

Collin et al., "Anodic Elecropolymerization of Films of Polypyrrole Functionalized with Metal Terpyridyl Redox Centres," *J. Electroanal: Chem.*, 286, 75-87, 1990.

Heineman et al., "Strategies For Electrochemical Immunoassay," *Anal. Chem.* 57 (12), 1321-1331, 1985.

Sanderson et al., "Filar Electrodes: Steady-State Currents and Spectroelectrochemistry at Twin Interdigitated Electrodes," *Anal. Chem.*, 57, 2388-2393, 1985.

Xu et al., "Heterogeneous Enzyme Immunoassay of Alpha-Fetoprotein in Maternal Serum by Flow-Injection Amperometric Detection of 4-Aminophenol," *Clin. Chem.*, 36 (11), 1941-1944, 1990.

Thompson et al. "Comparison of Methods for Following Alkaline Phosphatase Catalysis: Spectrophotometric versus Amperometric Detection,", *Anal. Biochem.*, 192, 90-95, 1991.

Wollenberger et al., "Interdigitated Array Microelectrodes for the Determination of Enzyme Activities," *Analyst*, 119, 1245-1249, Jun. 1994.

Wollenberger, "Electrochemical Biosensors—Ways to Improve Sensor Performance," *Biotechnology and Genetic Engineering Reviews*, 13, 27-266, Dec. 1995.

Pishko et al., "Direct Electrical Communication Between Graphite Electrodes and Surface Adsorbed Glucose Oxidase/Redox Polymer Complex," *Angew. Chem. Int. Ed. Engl.*, 29, (1), 82-84, 1990.

Garguilo et al., "Amperometric Sensors for Peroxide, Choline, and Acetylcholine Based on Electron Transfer Between Horseradish Peroxidase and a Redox Polymer," *Anal. Chem.*, 65, 523-528, 1993.

Ohara et al., "Glucose Electrodes Based on Cross-Linked $[Os(bpy)_2Cl]^{+/2+}$ Complexed Poly(1-Vinylimidazole) Films," *Anal Chem.*, 65, 3512-3517, 1993.

Paeschke et al., "Voltammetric Multichannel Measurements Using Silicon Fabricated Microelectrode Arrays," *Electroanalysis*, 8, (10), 891-898, 1996.

Matsue, "Electrochemical Sensors Using Microarray Electrodes,", *Trends Anal. Chem.*, 12 (3), 100-108, 1993.

Aoki et al., "Time-Dependence of Diffusion-Controlled Currents of a Soluble Redox Couple at Interdigitated Microarray Electrodes," *J. Electroanal. Chem.*, 266, 11-20, 1989.

$C_{49}H_{56}N_{10}O_3SOs$
F.W. 1055.30

SEQUENCE LISTING

```
<160> NUMBER OF SEQ ID NOS: 7

<210> SEQ ID NO 1
<211> LENGTH: 4
<212> TYPE: PRT
<213> ORGANISM: Homo sapiens
<220> FEATURE:
<221> NAME/KEY: CARBOHYD
<222> LOCATION: (1)..(1)
<223> OTHER INFORMATION: Glucose

<400> SEQUENCE: 1

Val His Leu Thr
1

<210> SEQ ID NO 2
<211> LENGTH: 5
<212> TYPE: PRT
<213> ORGANISM: Homo sapiens
<220> FEATURE:
<221> NAME/KEY: CARBOHYD
<222> LOCATION: (1)..(1)
<223> OTHER INFORMATION: Glucose
<220> FEATURE:
<221> NAME/KEY: SITE
<222> LOCATION: (5)..(5)
<223> OTHER INFORMATION: N-terminal 6(N-maleimido)hexanoyl

<400> SEQUENCE: 2

Val His Leu Thr Lys
1               5

<210> SEQ ID NO 3
<211> LENGTH: 5
<212> TYPE: PRT
<213> ORGANISM: Homo sapiens
<220> FEATURE:
<221> NAME/KEY: CARBOHYD
<222> LOCATION: (1)..(1)
<223> OTHER INFORMATION: glucose
```

```
<400> SEQUENCE: 3

Val His Leu Thr Lys
1               5

<210> SEQ ID NO 4
<211> LENGTH: 5
<212> TYPE: PRT
<213> ORGANISM: Homo sapiens
<220> FEATURE:
<221> NAME/KEY: CARBOHYD
<222> LOCATION: (1)..(1)
<223> OTHER INFORMATION: Glucose

<400> SEQUENCE: 4

Val His Leu Thr Cys
1               5

<210> SEQ ID NO 5
<211> LENGTH: 4
<212> TYPE: PRT
<213> ORGANISM: Homo sapiens

<400> SEQUENCE: 5

Val His Leu Thr
1

<210> SEQ ID NO 6
<211> LENGTH: 5
<212> TYPE: PRT
<213> ORGANISM: Homo sapiens

<400> SEQUENCE: 6

Val His Leu Thr Cys
1               5

<210> SEQ ID NO 7
<211> LENGTH: 5
<212> TYPE: PRT
<213> ORGANISM: Homo sapiens

<400> SEQUENCE: 7

Val His Leu Thr Lys
1               5
```

REDOX REVERSIBLE BIPYRIDYL-OSMIUM COMPLEX CONJUGATES

CROSS REFERENCE TO RELATED APPLICATIONS

This application is a divisional of U.S. application Ser. No. 09/322,791, filed May 28, 1999, now U.S. Pat. No. 6,352,824, which claims priority under 35 U.S.C. § 119(e) to U.S. Provisional Ser. No. 60/087,576, filed Jun. 1, 1998, which is expressly incorporated by reference.

FIELD OF THE INVENTION

This invention relates to novel redox-reversible conjugates. More particularly the invention is directed bipyridyl complexed-osmium conjugates useful for detection and quantification of biologically significant analytes in a liquid sample.

BACKGROUND AND SUMMARY OF THE INVENTION

Therapeutic protocols used today by medical practitioners in treatment of their patient population requires accurate and convenient methods of monitoring patient disease states. Much effort has been directed to research and development of methods for measuring the presence and/or concentration of biologically significant substances indicative of a clinical condition or disease state, particularly in body fluids such as blood, urine or saliva. Such methods have been developed to detect the existence or severity of a wide variety of disease states such as diabetes, metabolic disorders, hormonal disorders, and for monitoring the presence and/or concentration of ethical or illegal drugs. More recently there have been significant advancements in the use of affinity-based electrochemical detection/measurement techniques which rely, at least in part, on the formation of a complex between the chemical species being assayed (the "analyte") and another species to which it will bind specifically (a "specific binding partner"). Such methods typically employ a labeled ligand analog of the target analyte, the ligand analog selected so that it binds competitively with the analyte to the specific binding partner. The ligand analog is labeled so that the extent of binding of the labeled ligand analog with the specific binding partner can be measured and correlated with the presence and/or concentration of the target analyte in the biological sample.

Numerous labels have been employed in such affinity based sample analysis techniques, including enzyme labeling, radioisotopic labeling, fluorescent labeling, and labeling with chemical species subject to electrochemical oxidation and/or reduction. The use of redox reversible species, sometimes referred to as electron transfer agents or electron mediators as labels for ligand analogs, have proven to provide a practical and dependable results in affinity-based electrochemical assays. However, the use of electrochemical techniques in detecting and quantifying concentrations of such redox reversible species (correlating with analyte concentrations) is not without problem. Electrochemical measurements are subject to many influences that affect the accuracy of the measurements, including not only those relating to variations in the electrode structure itself and/or matrix effects deriving from variability in liquid samples, but as well those deriving from interference between multiple electroactive species, especially when assay protocols require detection or quantification of multiple electroactive species.

The present invention relates to novel diffusible, redox-reversible osmium-bipyridyl conjugates useful in immunosensors based on either indirect amplified electrochemical detection techniques or on direct electrochemical measurement of detectable species with microarray electrodes under bipotentiostatic control. An Os-bipyridyl complex can, for example be covalently attached to a peptide which has amino acid sequence of the binding epitope for an antibody. When Os complex/peptide conjugate is bound to antibody, the conjugate does not function electrochemically; it is said to be "inhibited". Typically an analyte present in sample will compete with Os-bipyridyl complex/peptide conjugate for the limited number of binding sites on the antibody. When more analyte is present, more free Os-bipyridyl complex/peptide conjugate will be left in an unbound diffusible state producing higher current at a sensor electrode, i.e. one of the working electrodes where measured events (oxidation or reduction) are taking place. In the opposite case, when less analyte is present, more indicator/peptide conjugate will be bound to antibody resulting less free conjugates and producing lower current levels at the working electrodes. Therefore the current detected at either one of the working electrodes will be a function of analyte concentration.

It is frequently desired to measure more than one analyte species in a liquid sample. Measurement of multiple species in a mixture has been achieved with photometry and fluorescence, via selection of the appropriate wavelengths. Electrochemical measurements of a single species in a complex mixture are routinely made by selecting a potential at which only the desired species is oxidized or reduced (amperometry) or by stepping or varying the potential over a range in which only the desired species changes its electrochemical properties (AC and pulse methods). These methods suffer from disadvantages including lack of sensitivity and lack of specificity, interference by charging and matrix polarization currents (pulse methods) and electrode fouling due to the inability to apply an adequate over potential. Moreover, electrochemical measurements are complicated by interference between the multiplicity of electroactive species commonly extant in biological samples.

Electrode structures which generate steady state current via diffusional feedback, including interdigitated array electrodes (IDAs) (FIGS. 1 and 2) and parallel plate arrangements with bipotentiostatic control are known. They have been used to measure reversible species based on the steady state current achieved by cycling of the reversible species. A reversible mediator (redox reversible species) is alternately oxidized and reduced on the interdigitated electrode fingers. The steady state current is proportionate to mediator concentration (FIG. 3) and limited by mediator diffusion. A steady state current is achieved within seconds of applying the predetermined anodic (more positive) and cathodic (less positive or negative) potentials (FIG. 6) to the microelectrode array. The slope of a plot of the IDA current vs. mediator concentration is dependent on IDA dimensions, and the slope increases with narrower electrode spacings (FIG. 7).

The present invention provides novel osmium-bipyridyl complex conjugates useful in a method for measuring multiple analyte species in the same sample, and optimally on the same electrode structure, thus improving the accuracy of the relative measurements. The present conjugates can be used with other electroactive conjugate species having unique redox potentials to provide an electrochemical biosensor with capacity to provide improved accuracy. Analyte concentration can be measured/calculated from electrometric data obtained on the same liquid sample with the same electrode structure, thereby minimizing perturbations due to variability in sample or electrode structure.

The diffusible osmium conjugates of this invention find use in assay based on the principle of diffusional recycling, where a diffusible redox reversible species is alternately oxidized and reduced at nearby electrodes (the working electrodes), thereby generating a measurable current. As alternate oxidation and reduction is required for measurement, only electroactive species which are electrochemically reversible at the predetermined redox potential are measured thereby eliminating, or at least reducing, the impact or interference from non-reversible electroactive species in the sample or other reversible-redox species having unique (at least 50 millivolts different) redox potential. Redox reversible species having different oxidation potentials can be independently measured in a mixture by selecting and bipotentiostatically controlling the oxidizing and reducing potentials for neighboring electrode pairs so that only the species of interest is oxidized at the anode and reduced at the cathode. When the working electrodes are dimensioned to allow diffusional recycling of the redox-reversible-species at the selected oxidizing and reducing potentials appropriate for that species, a steady state current is quickly established through the sample and the electrode structure. The magnitude of the current at the working electrodes where the measurable oxidative and reductive events are taking place, is proportional to the concentration of the diffusible redox reversible species in the sample. When two or more redox reversible species are utilized, they are selected to have redox potentials differing by at least 50 millivolts, most preferably at least 200 millivolts, to minimize interference between one species and the other in measurements of the respective steady state currents. The present osmium complex conjugates have unique redox potentials that allow them to be used with/in the presence of other electroactive conjugates without (or with minimal) interference.

The present conjugates can be used in any electrode structure/system which allows for diffusional recycling to achieve steady state current in response to application of pre-selected complex species-specific anodic and cathodic potentials. Suitable electrode structures include interdigitated array microelectrodes and parallel plate electrodes separated by distances within the diffusion distance of the respective redox reversible species. The electrode structures typically include a reference electrode (e.g., Ag/AgCl), at least two working electrodes, and optionally an auxiliary electrode for current control. In use, a programmable bipotentiostat is placed in electrical communication with the electrode structure for applying the respective anodic and cathodic potentials specific for each of the respective redox reversible species utilized in the method/biosensor. Several novel osmium complexes including those of this invention have been developed for use as labels for preparing ligand analog conjugates having potential differences sufficient (at least 50 millivolts) to allow the use of two osmium complexes (as opposed to an osmium complex and a ferrocene or other redox reversible label) in multiple conjugate based electrochemical assays.

The present osmium conjugates are useful in a method for measuring the concentration of one or more analytes in a liquid sample. The method includes contacting a portion of the sample with pre-determined amounts of at least a first and second redox reversible species having a redox potential differing by at least 50 millivolts from that of each other species. Each respective species comprises a liquid sample diffusible conjugate of a ligand analog of an analyte in the liquid sample and a redox reversible label. The liquid sample is also contacted with a predetermined amount of at least one specific binding partner for each analyte to be measured. The diffusible conjugate is selected so that it is capable of competitive binding with the specific binding partner for said analyte. The concentration of the diffusible redox-reversible-species in the liquid sample is then determined electrochemically. The sample is contacted with an electrode structure, including a reference electrode and at least first and second working electrodes dimensioned to allow diffusional recycling at least one of the diffusible redox-reversible-species in the sample, when a predetermined redox-reversible-species-dependent cathodic potential is applied to one working electrode and a predetermined redox-reversible-species-dependent anodic potential is applied to the second working electrode. Typically, a first cathodic potential is applied to the first working electrode and a first anodic potential is applied to the second working electrode to establish current flow through the sample due to diffusional recycling of the first redox-reversible-species without significant interference from the second redox-reversible-species. Current flow through one or more of the electrodes at the first anodic and cathodic potentials is measured.

Similarly current flow responsive to application of second cathodic and anodic potentials to electrodes in contact with the sample is measured and correlated with measured current flows for known concentrations of the respective redox-reversible-species, said concentrations being proportionate to the respective analyte concentrations.

The reagent components including the present bipyridyl-osmium conjugates of the invention and the specific binding partners, can be provided in the form of a test kit for measuring the targeted analyte(s) in a liquid sample, either as separate reagents or, more preferably, combined as a multi-reagent composition, e.g. combined redox reversible species, combined specific binding partners, or combined redox reversible species and specific binding partners. The kit optionally, but preferably, includes an electrode structure dimensioned to allow diffusional redox recycling of diffusible redox reversible species in the liquid sample. The electrode structure includes conductors for connecting the structure to a bipotentiostat programmed to apply redox-reversible-species-dependent-anodic and cathodic potentials to the electrode structure and to sense and measure current flow, typically at one or both of the working electrodes, responsive to such potentials.

This invention is based on the preparation and use of novel electrochemically detectable osmium complexes and covalent conjugates of said complexes having oxidation potentials differing sufficiently from other redox-reversible complexes to enable their use together with other osmium or other metal conjugates. Thus, there are provided novel osmium labeled ligand analogs capable of binding to a specific binding partner of a biologically significant analyte. The electrochemically detectable osmium conjugates comprise a tris(bipyridyl) osmium complex characterized by fast mediation kinetics and low redox potential (+150 mV vs. Ag/AgCl). Another group of osmium complex labeled, electrochemically detectable conjugates that can be used with the present complexes in multi-conjugate assay protocols include bis(bipyridyl) imidazoyl haloosmium complexes, which, like the tris(bipyridyl) osmium complexes are characterized by fast mediation kinetics, but the tris(bipyridyl) complexes have a redox potential sufficiently different from the bis(pyridyl) imidazolyl chloroosmium complexes to allow their use together in assays utilizing microelectrode arrays for measuring more than one analyte in a single liquid sample by concentration dependent currents amplified by diffusional redox recycling.

The present osmium complex conjugates can be used in combination with another conjugated redox-reversible-species for the measurement of both glycosylated hemoglobin and hemoglobin in a lysed blood sample. One redox-reversible-species preferably comprises an imidazole-osmium complex covalently linked to a ligand analog of either hemoglobin or glycosylated hemoglobin, and a second redox-reversible-species comprising a second redox reversible label covalently bound to a ligand analog of the other of the two target analytes. The method enables measurement of the concentration of both the glycosylated hemoglobin (HbAlc) and the concentration of either total hemoglobin or that of unglycosylated hemoglobin ($HbA_0$) thereby enabling calculation of the results as a ratio of the two measurements (% HbAlc). It is advantageous to assay both HbAlc and total hemoglobin (or $HbA_0$) using the same principle in a single sample, particularly because ratioing works minimize biases due to environmental effects.

DETAILED DESCRIPTION OF THE INVENTION

Figure 2:
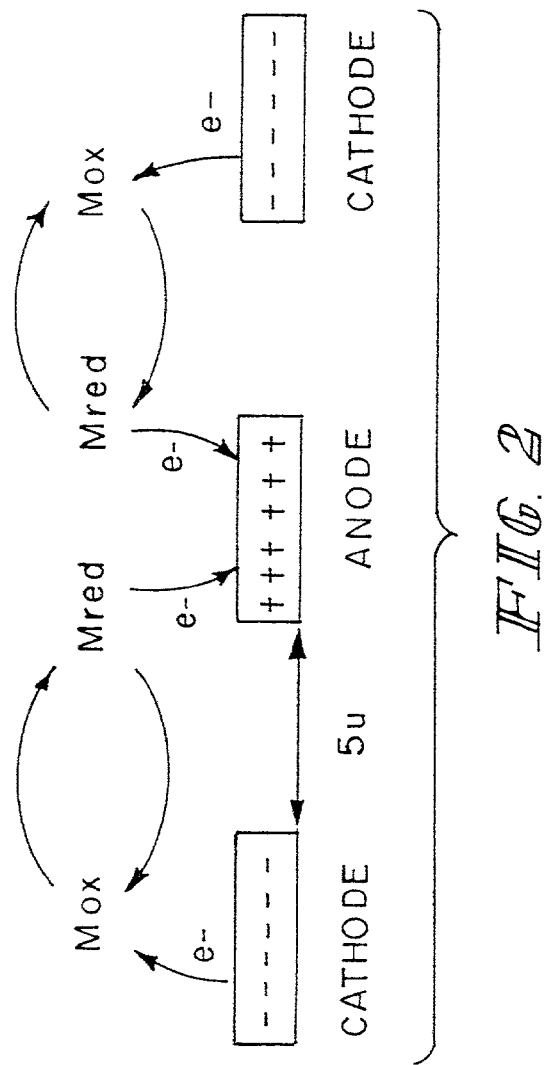
FIG. 2 is a partial cross-sectional view of the electrode of FIG. 1 illustrating the conditions of steady state current limited by diffusion of mediator (M).

The diffusible redox reversible species of this invention is a liquid-sample-diffusible conjugate of a ligand analog of an analyte and a redox reversible bipyridyl-osmium complex. The term "redox reversible" as used herein refers to a chemical species capable of reversible oxidation and reduction in a liquid sample. Redox reversible labels are well-known in the art and include ligand complexes of transition metal ions, for example iron (ferrocene and ferrocene derivatives), ruthenium and osmium. The conjugate is prepared by linking the ligand analog to the label either covalently through difunctional linking agents or by combination of covalent linkages and art-recognized specific binding entities (for example, biotin-avidin).

More particularly, the present invention is directed to a redox reversible osmium complex of the formula

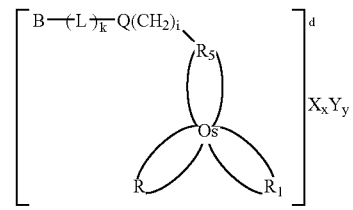

wherein

R and $R_1$ are the same or different and are 2,2'-bipyridyl, 4,4'-disubstituted-2,2'-bipyridyl, 5-5'-disubstituted,-2,2'-bipyridyl, 1,10-phenanthrolinyl, 4,7-disubstituted-1,10-phenanthrolinyl, or 5,6-disubstituted-1,10-phenanthrolinyl, wherein each substituent is a methyl, ethyl, or phenyl group, $R_5$ is 4-substituted-2,2'-bipyridyl or 4,4'-disubstituted-2,2'-bipyridyl wherein the 4-substituent is the group $B-(L)_k-Q(CH_2)_i-$ and the 4'-substituent is a methyl, ethyl or phenyl group;

R, $R_1$ and $R_5$ are coordinated to Os through their nitrogen atoms;

Q is O, S, or $NR_4$ wherein $R_4$ is hydrogen, methyl or ethyl;

—L— is a divalent linker;

k is 1 or 0;

i is 1, 2, 3, 4, 5 or 6;

B is hydrogen or a group comprising a ligand capable of binding to a specific binding partner;

d is +2 or +3;

X and Y are anions selected from monovalent anions, chloride, bromide, iodide, fluoride, tetrafluoroborate, perchlorate, and nitrate and divalent anions, e.g., sulfate, carbonate or sulfite wherein x and y are independently 0, 1, 2, or 3 so that the net charge of $X_xY_y$ is −2 or −3.

Another redox reversible osmium complex that can be used with the present imidazole-osmium conjugates is a compound of the formula

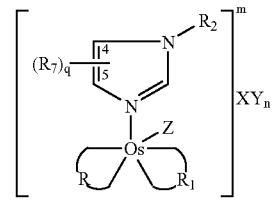

wherein

R and $R_1$ are the same or different and are 2,2'-bipyridyl, 4,4'-disubstituted-2,2'-bipyridyl, 5-5'-disubstituted,-2,2'-bipyridyl, 1,10-phenanthrolinyl, 4,7-disubstituted-1,10-phenanthrolinyl, or 5,6-disubstituted-1,10-phenanthrolinyl, wherein each substituent is a methyl, ethyl, or phenyl group, R and $R_1$ are coordinated to Os through their nitrogen atoms;

q is 1 or 0;

$R_7$ is B-$(L)_k$-Q$(CH_2)_i$—;

$R_2$ is hydrogen, methyl, or ethyl when q is 1, and $R_2$ is B-$(L)_k$-Q$(CH_2)_i$—when q is 0; wherein in the group B-$(L)_k$-Q$(CH_2)_i$-Q is O, S, or $NR_4$ wherein $R_4$ is hydrogen, methyl or ethyl; —L— is a divalent linker;

k is 1 or 0;

i is 1, 2, 3, 4, 5 or 6; and

B is hydrogen or a group comprising a ligand capable of binding to a specific binding partner;

Z is chloro or bromo;

m is +1 or +2;

X is monovalent anion, e.g., chloride, bromide, iodide, fluoride, tetrafluoroborate, perchlorate, nitrate, or a divalent anion, e.g., sulfate, carbonate, or sulfite;

Y is monovalent anion, e.g., chloride, bromide, iodide, fluoride, tetrafluoroborate, perchlorate or nitrate; and n is 1 or zero, provided that when X is a divalent anion, n is zero, and when m is 1, n is zero and X is not a divalent anion.

Figure 8:
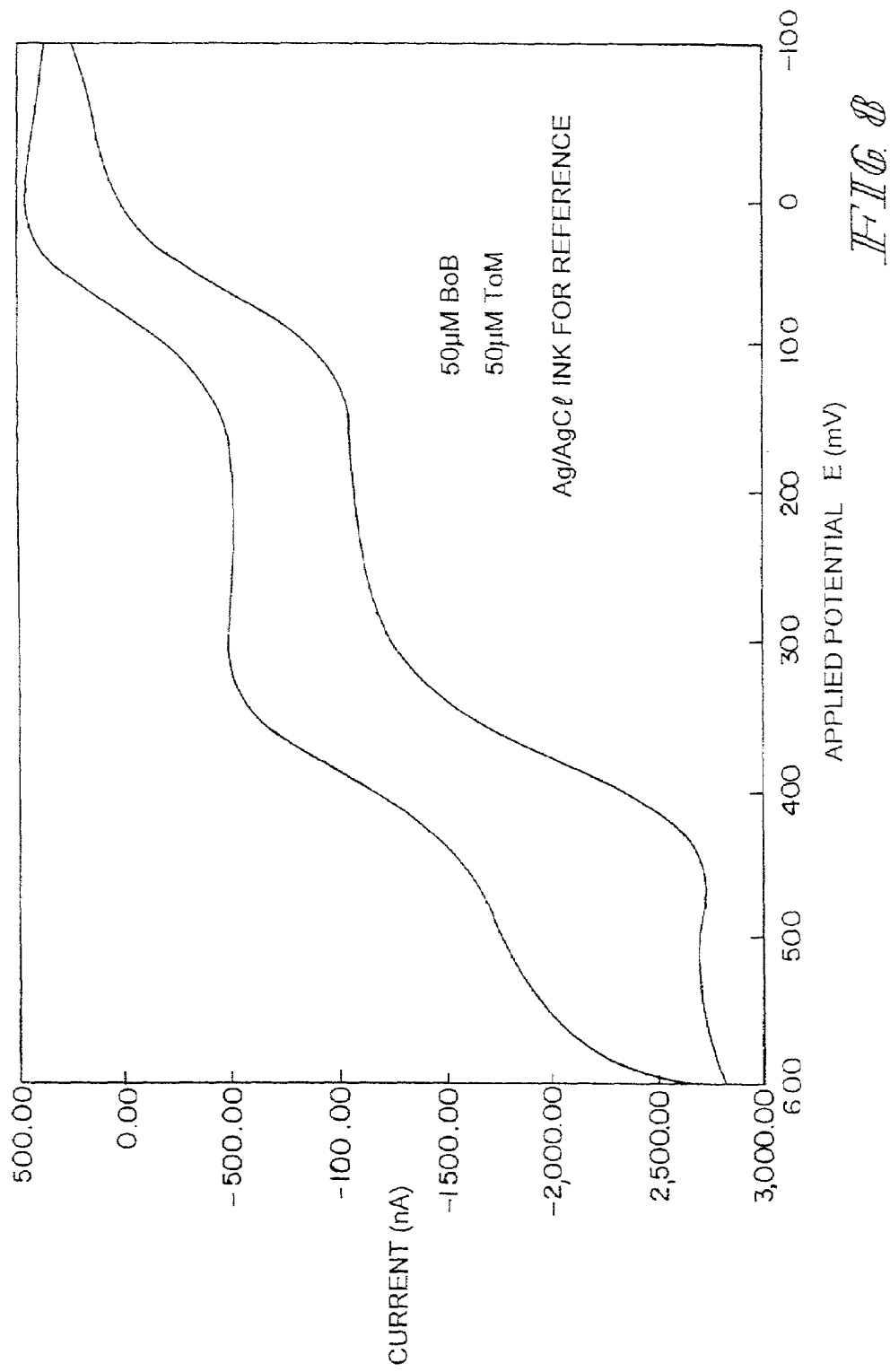
FIG. 8 is a graphic illustration of current flow as a function of applied potential for a liquid sample containing equimolar (50 µM) of a bis-(bipyridyl) imidazolyl chloroosmium complex and a tris(bipyridyl) osmium complex of this invention.

Redox reversible conjugate species of each of those formulas are prepared from the corresponding compounds wherein k is 0 and B is hydrogen by reacting such compounds with either a heterofunctional crosslinker of the formula S-L'-T wherein L' is a divalent linker and S and T are different electrophilic groups capable of reacting with a nucleophilic group to form a covalent bond, or with a homofunctional crosslinker of the formula S-L'-T wherein L' is a divalent linker and S and T are the same electrophilic groups capable of reacting with a nucleophilic group to form a covalent bond. The resulting products are then reacted with ligand analogs using classical coupling reaction conditions to product the conjugate species. The oxidizing potentials of the respective bis(bipyridyl) imidazolyl and tris(bipyridyl) osmium complexes defined above is such that the respective complexes can be used as reversible redox labels for the respective redox reversible species in performance of the method. FIG. 8 illustrates a cyclic voltammogram for a liquid sample containing equimolar (50 μM) amounts of a bis(bipyridyl) imidazolyl chloroosmium complex and a tris (bipyridyl) osmium complex.

In one embodiment of the invention the specific binding partner for each analyte is an antibody and the ligand analog is selected so that it binds competitively with the analyte to the antibody. There are, however, other examples of ligand-specific binding partner interactions that can be utilized in developing applications of the present method. Examples of ligands and specific binding partners for said ligands are listed below.

| Ligand | Specific Binding Partner |
| --- | --- |
| Antigen (e.g., a drug substance) | Specific antibody |
| Antibody | Antigen |
| Hormone | Hormone receptor |
| Hormone receptor | Hormone |
| Polynucleotide | Complementary polynucleotide strand |
| Avidin | Biotin |
| Biotin | Avidin |
| Protein A | Immunoglobulin |
| Immunoglobulin | Protein A |
| Enzyme | Enzyme cofactor (substrate) |
| Enzyme cofactor (substrate) | Enzyme |
| Lectins | Specific carbohydrate |
| Specific carbohydrate of lectins | Lectins |

The term "antibody" refers to (a) any of the various classes or subclasses of immunoglobulin, e.g., IgG, IgM, derived from any of the animals conventionally used, e.g., sheep, rabbits, goats or mice; (b) monoclonal antibodies; (c) intact molecules or "fragments" of antibodies, monoclonal or polyclonal, the fragments being those which contain the binding region of the antibody, i.e., fragments devoid of the Fc portion (e.g, Fab, Fab', F(ab')$_2$) or the so-called "half-molecule" fragments obtained by reductive cleavage of the disulfide bonds connecting the heavy chain components in the intact antibody. The preparation of such antibodies are well-known in the art.

The term "antigen" used in describing and defining the present invention includes both permanently antigenic species (for example, proteins, peptides, bacteria, bacteria fragments, cells, cell fragments and viruses) and haptans which may be rendered antigenic under suitable conditions.

The present osmium labeled conjugates are useful alone or in combination with other conjugates in methods for measuring the concentration of one or more analytes in a liquid sample. One method enables two or more independent amperometric measurements of the sample on a single electrode structure. The method comprises contacting a volume of said liquid sample with
1) predetermined amounts of at least a first and second redox reversible species, each respective species having a redox potential differing by at least 50 millivolts from that of each other species, at least one species comprising a liquid sample diffusible conjugate of a ligand analog of an analyte in the liquid sample and a redox reversible label, said conjugate capable of competitive binding with a specific binding partner for said analyte, and
2) a predetermined amount of at least one specific binding partner for each analyte to be measured; and
electrochemically determining the concentration of each of said diffusible redox-reversible species in the liquid sample by
contacting said sample with an electrode structure including a reference electrode and at least first and second working electrodes dimensioned to allow diffusional recycling of the diffusible redox reversible species in the sample when a predetermine redox-reversible-species-dependent cathodic potential is applied to one working electrode and a predetermined redox-reversible-species-dependent anodic potential is applied to a second working electrode, said diffusional recycling of said species being sufficient to sustain a measurable current through said sample,
applying a first cathodic potential to the first working electrode and a first anodic potential to the second working electrode, said first cathodic and anodic potentials corresponding to those respective potentials necessary to establish current flow through the sample due to diffusional recycling of the first redox reversible species without significant interference from said second redox reversible species, measuring current flow at said first anodic and cathodic potentials, applying a second cathodic potential to said first or second working electrode and a second anodic potential to the other working electrode, said second cathodic and anodic potential corresponding to those respective potentials necessary to establish current flow through the sample due to diffusional recycling of the second redox-reversible-species without significant interference from the first redox reversible species, measuring current flow at said second anodic and cathodic potentials, and correlating the respective measured current flows to that for known concentrations of the respective diffusible redox reversible species, said concentrations being proportionate to the respective analyte concentrations.

That method has very broad applicability but in particular may be used to assay: drugs, hormones, including peptide hormones (e.g., thyroid stimulating hormone (TSH), luteinizing hormone (LH), follicle stimulating hormone (FSH), insulin and prolactin) or non-peptide hormones (e.g, steroid hormones such as cortisol, estradiol, progesterone and testosterone, or thyroid hormones such as thyroxine (T4) and triiodothyronine), proteins (e.g., human chorionic gonadotropin (hCG), carcino-embryonic antigen (CEA) and alphafetoprotein (AFP)), drugs (e.g., digoxin), sugars, toxins or vitamins.

The method can be performed on liquid samples comprising biological fluids such as saliva, urine, or blood, or the liquid sample can be derived from environmental sources. The liquid samples can be analyzed "as is," or they can be diluted, buffered or otherwise processed to optimize detection of the targeted analyte(s). Thus, for example, blood samples can be lysed and/or otherwise denatured to solubilize cellular components.

The method can be performed using widely variant sampling handling techniques. Thus, the sample can be pre-mixed with either or both of the specific binding partner for the targeted analytes and the redox reversible species prior to contacting the sample with the electrode structure, or the liquid sample, either neat or pre-processed, can be delivered to a vessel containing predetermined amounts of the redox reversible species and the specific binding partner for subsequent or simultaneous contact with the electrode structure. The order of introduction of the components into the sample is not critical; however, in one embodiment of the invention the predetermined amounts of the specific binding partners are first added to the sample, and thereafter, there is added the predetermined amounts of the redox reversible species. It is also possible to combine the predetermined amounts of the specific binding partners with the redox reversible species to form the respective complexes prior to combining those components with the liquid sample. In that latter case the redox reversible species will be displaced from its respective specific binding partner by the corresponding analyte to provide a concentration of the redox reversible species proportionate to the concentration of analyte in the liquid sample. The reagents, that is, the predetermined amounts of the specific binding partner of each analyte and the predetermined amounts of the corresponding redox reversible species can, for example, be deposited in a vessel for receiving a predetermined volume of the liquid sample.

The liquid sample is added to the vessel, and thereafter, or simultaneously, the liquid sample is contacted with the electrode structure.

Figure 1:
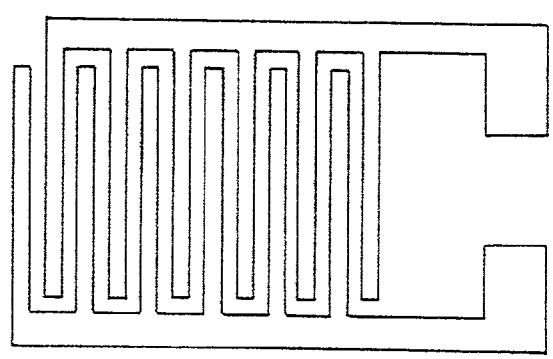
FIG. 1 is an enlarged plan view of an interdigitated array electrode for reversible mediator measurement.
Figure 3:
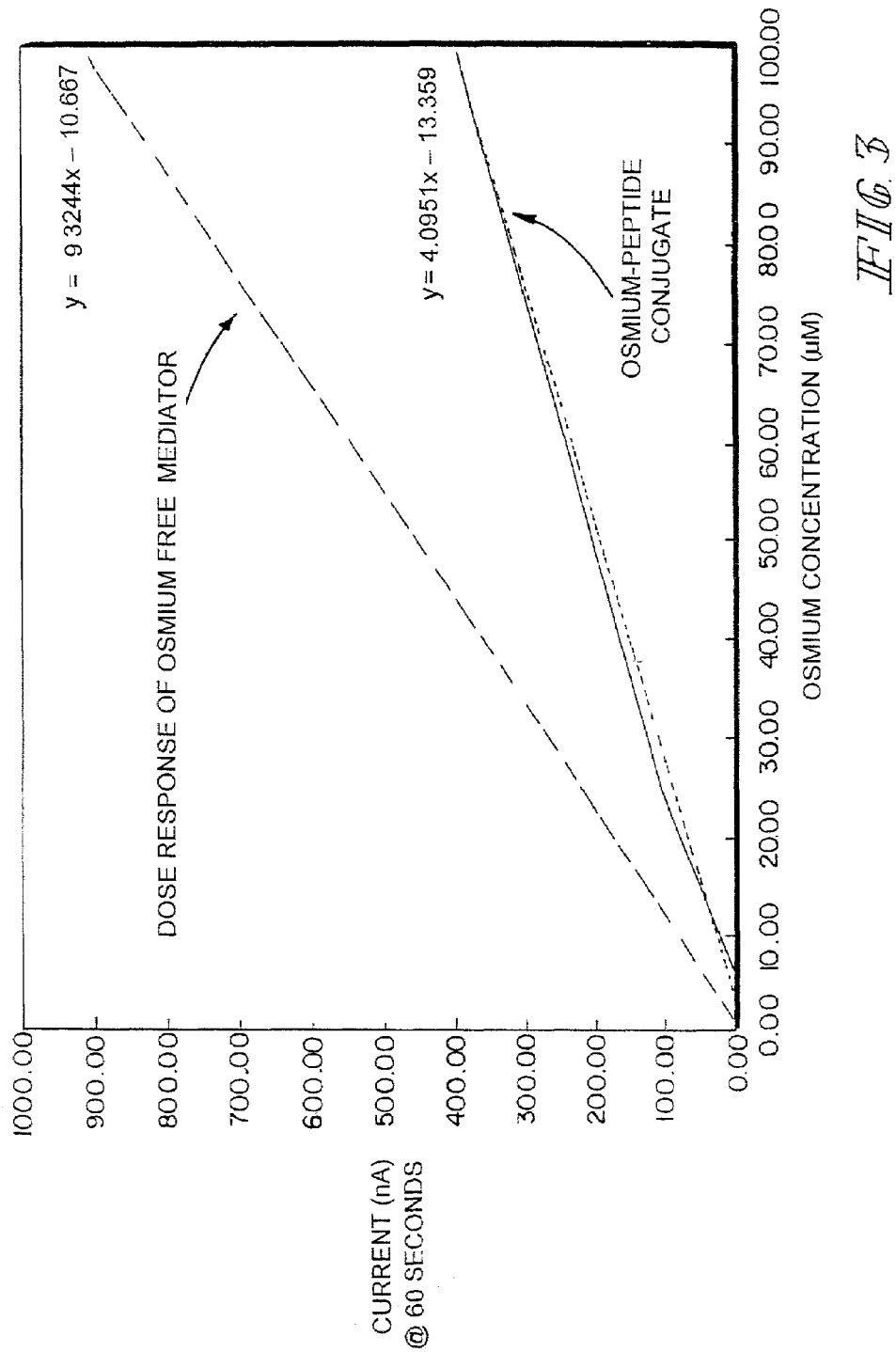
FIG. 3 is a graphic presentation of dose response currents for a bis-(bipyridyl) imidazolyl chloroosmonium mediator peptide conjugate.

The electrode structure includes a reference electrode and at least first and second working electrodes dimensioned to allow diffusional recycling of the diffusible redox reversible species in the sample when predetermined redox-reversible-species-dependent-cathodic and anodic potential is applied to the working electrodes. The term "working electrode" as used herein refers to an electrode where measured events (i.e. oxidation and/or reduction) take place and resultant current flow can be measured as an indicator of analyte concentration. "Anodic potential" refers to the more positive potential (applied to the anode) and "cathodic potential" refers to the less positive or negative potential applied to the cathode (vs a reference electrode). Electrodes dimension to allow diffusional recycling are well known in the art and are typically in the form of arrays of microdiscs, microholes, or microbands. In one embodiment the electrodes are in the form of an interdigitated arrangement of microband electrodes with micron or submicron spacing. Short average diffusional length and a large number of electrodes are desirable for effective current amplication by recycling of reversible redox species. The microelectrode arrays can be fabricated, for example, as pairs of interdigitated thin film metal electrodes in micron and submicron geometry arranged on an insulator substrate, for example, oxidized silicon. Each of the electrode fingers (FIG. 1) are spaced from its neighboring finger in the nanometer to low micrometer (1–10 microns) range. Microelectrode arrays can be fabricated using photolithography, electron bean lithography, and so-called lift-off technique. Thus, an interdigitated electrode array (IDA) can be deposited on glass, silicon or polyamide utilizing the following general procedure:

1. Grow thermal oxide layer on silicon substrate;
2. Sputter 400 Å chromium seed layer, 2000 Å gold;
3. Spin-coat and soft-bake photo resist;
4. Expose and develop photo resist with IDA pattern;
5. Pattern gold and chromium with ion beam milling;
6. Strip photo resist; and
7. Cut electrodes into chips by first coating with a protective layer, cutting into strips, stripping the protective layer, and cleaning electrode surfaces in oxygen plasma.

The electrode structure can be formed on an inner surface of a chamber for receiving the liquid sample, e.g., a cuvette, a capillary fill chamber, or other sample receiving vessel wherein the electrode structure can be contacted with the liquid sample. Alternatively, the electrode structure can form part of a probe for dipping into the liquid sample after the sample has been contacted with the predetermined amounts of the redox reversible species and the specific binding partners. The electrode structure is in contact with conductors that enable application of the respective cathodic and anodic potentials for carrying out the present method. The anodic and cathodic potentials are applied relative to a reference electrode component of the electrode structure using a bipotentiostat. The electrode structure can optionally include an auxiliary electrode for current control. The bipotentiostat is utilized to apply a first cathodic potential to a first working electrode and a first anodic potential to a second working electrode, the first cathodic and anodic potentials corresponding to those respective potentials necessary to establish current flow through the sample due to diffusional recycling of the first redox reversible species. Optionally the potential on one working electrode can be set at a first diffusible species dependent, anodic potential and current flow is measured as the potential of the other working electrode is swept through a potential corresponding to the predetermined diffusible species dependent cathodic potential (or vice versa).

The cathodic and anodic potentials appropriate for each reversible redox species can be readily determined by empirical measurement. The multiple redox reversible species used in performance of the method of this invention are selected to have redox potentials differing by at least 50 millivolts, more preferably at least 100 millivolts, more preferably at least 200 millivolts, from that of each other redox reversible species utilized in the method. The difference in redox potentials of the redox reversible species being used allow each species to be detected without significant interference from the second or any other redox reversible species in the liquid sample. A steady state current flow is rapidly established at each of the working electrodes following application of the anodic and cathodic potentials. Current flow can be measured at either or both working electrodes, and it is proportionate to the concentration of the recycling redox reversible species.

Second cathodic and anodic potentials are applied to the working electrodes wherein said second potentials correspond to those respective potentials necessary to establish current flow through the sample due to diffusional recycling of the second redox reversible species without significant interference from the first redox reversible species, and the resulting steady state current flow is measured. This step is repeated for each redox reversible species utilized in the method. The measured current flows are then correlated to known concentrations of the respective diffusible redox reversible species. Those concentrations are proportionate to the respective analyte concentrations.

The method steps can be conducted using a programed bipotentiostat to control potentials on the electrode structure in contact with the sample. The bipotentiostat can be included either in a desktop or hand-held meter further including means for reading values for steady state current, storing said values, and calculating analyte concentrations using a microprocessor programmed for making such calculations.

The relative amounts of the first and second redox reversible species and the respective specific binding partners for the targeted analytes to be measured in the method can be determined empirically. They are dependent on the concentration ranges of the targeted analyte, and the binding stoichiometry of the specific binding partner, the binding constant, the analyte and the corresponding redox reversible species. The amounts of each reagent appropriate for each analyte being measured can be determined by empirical methods.

The present osmium conjugates can also be used in a method for measuring two proteinaceous analytes in a liquid sample wherein the ligand analog component of the first redox reversible species is a peptide comprising an epitope of a first analyte and the ligand analog component of a second redox reversible species is a peptide comprising an epitope of a second analyte. One specific binding partner utilized in the method is an antibody recognizing the epitope of the first analyte, and the other specific binding partner is an antibody recognizing the epitope of the second analyte. In another application of that method two independent measurements are performed on a single analyte in a liquid sample. In that embodiment the respective ligand analog component of the first and second redox reversible species are different ligand analogs of the targeted analyte. Where the targeted analyte is a proteinaceous compound, the ligand analog component of the first redox reversible species is a peptide comprising a first epitope of the analyte, and the ligand analog of the second redox reversible species is a peptide comprising a second epitope of the analyte, and the specific binding partners are first and second antibodies, each recognizing respective first and second analyte epitopes.

The present osmium conjugates can also be used in a device for detecting or quantifying one or more analytes in a liquid sample. The device comprises at least two redox reversible species, each capable of diffusion in said liquid sample at least in the presence of a respective predetermined analyte, said redox reversible species having respective redox potentials differing by at least 50 millivolts, an electrode structure for contact with the liquid sample in said chamber, said electrode structure including a reference electrode and working electrodes dimensioned to allow diffusional recycling of a diffusible redox reversible species in a liquid sample in contact with the electrode system when a predetermined redox-reversible-species-dependent cathodic potential is applied to one working electrode and a predetermined redox-reversible-species-dependent anodic potential is applied to a second working electrode, said diffusional recycling of said species being sufficient to sustain measurable current through each working electrode, and conductors communicating with the respective electrodes for applying said anodic potential and said cathodic potential and for carrying the current conducted by the electrodes.

The device can be constructed using procedures and techniques that have been previously described in the art for construction of biosensors employing electrometric detection techniques. Thus, for example, the device can include a chamber that has a receiving port, and the chamber is dimensioned so that it fills by capillary flow when the liquid sample is contacted with the sample receiving port. The electrode structure can be formed on a plate that defines a wall of the chamber so that the electrode structure will contact a liquid sample in the chamber. Thus, for example, the device can be constructed using the general procedures and designs described in U.S. Pat. No. 5,141,868, the disclosure of which is expressly incorporated herein by reference. The features of the present invention can also be incorporated into other electrochemical biosensors or test strips, such as those disclosed in U.S. Pat. Nos. 5,120,420; 5,437,999; 5,192,415; 5,264,103; and 5,575,895, the disclosures of which U.S. patents are expressly incorporated herein by reference. The device can be constructed to include the predetermined amounts of the redox reversible species and the specific binding partners. For example, a mixture of such reagents can be coated onto a wall of the sample chamber in said device during device construction, so that the liquid sample is contacted with the reagent mixture as it is delivered into the chamber for containing the sample. In one embodiment the device is constructed for quantifying a first analyte and a second analyte in liquid sample. The device comprises two redox reversible species, a first redox reversible species comprising a conjugate of a ligand analog of the first analyte and a second redox reversible species comprising a conjugate of a ligand analog of the second analyte, and a specific binding partner for each analyte so that each of said analyte analog conjugates are capable of binding competitively with its respective analyte to a specific binding partner.

In another application of the present osmium conjugates, they are used in conjunction with a device that further comprises a bipotentiostat in electrical communication with the conductors for applying a redox- reversible-species-dependent-cathodic potential to one working electrode and a redox-reversible-species-dependent-anodic potential to a second working electrode. The biopotentiostat can be programmed to apply a sequence of potentials to the respective working electrodes. More particularly, the bipotentiostat can be programmed to apply first cathodic potential to a first working electrode and a first anodic potential to a second working electrode, said first anodic and cathodic potentials corresponding to those potentials necessary to establish current flow to the sample due to diffusional recycling of the first redox reversible species. The bipotentiostat is also programmed to apply a second cathodic potential to said first working electrode and a second potential to the second anodic electrode, said second cathodic and anodic potentials corresponding to those potentials necessary to establish current flow through the sample due to diffusional recycling of the second redox reversible species. In an alternate embodiment the device includes first and second redox reversible species, and at least first and second electrode structures for contact with the liquid sample in the chamber, each of said electrode structures comprising a microarray of working electrodes, and means for switching the bipotentiostat between the first and second electrode structures. In preferred device embodiments there is provided means for measuring current flow through the sample at each of the first and second potentials and preferably storing values for said current flows in a register coupled to a microprocessor programmed to calculate analyte concentrations based on said values.

In still another embodiment the present conjugate is used in a kit for measuring the concentration of one or more analytes in liquid sample. The kit comprises at least two redox reversible species for contact with the liquid sample, each capable of diffusion in the liquid sample at least in the presence of a predetermined analyte, at least one of such species being a conjugate of a ligand analog of an analyte and a redox reversible label, said redox reversible species having respective redox potentials differing by at least 50 millivolts;

a specific binding partner for each analyte;

an electrode structure for contact with the liquid sample, said electrode structure including a reference electrode and working electrodes dimensioned to allow diffusional recycling of diffusible redox reversible species in the sample when a predetermined redox-reversible-species-dependent-cathodic potential is applied to one working electrode and a predetermined redox-reversible-species-dependent-anodic potential is applied to the second working electrode, said diffusional recycling of said species means sufficient to sustain a measurable current through the sample; and conductors communicating with the respective electrodes for applying said anodic potential and said cathodic potential and for carrying the current conducted by the electrodes.

In one embodiment, the present redox reversible conjugate species are mixed with other electroactive species as a novel composition for contact with the liquid sample. In another embodiment each of the redox reversible species and the specific binding partner for each analyte is mixed as a novel composition for contact with the liquid sample. Preferably, the redox reversible label of at least one of the redox reversible species comprises an osmium complex of this invention.

Preparation of Os Mediator Labels

The Os mediator bis(bipyridyl) imidazolyl chloroosmium has been shown to be an excellent electron mediator for many oxide-reductase enzymes (U.S. Pat. No. 5,589,326). It has fast mediation kinetics (about 500 times faster than ferricyanide with glucose oxidase) and a relatively low redox potential (+150 mV vs. Ag/AgCl). It has also very fast electron transfer rate at electrode surface. More importantly, the organic ligands on Os mediator can be functionalized so that it can be covalently linked to other molecules without detrimental effects on redox properties of the Os center. These unique properties of Os mediator make it an ideal electrochemical indicator for sensors based on immunoaffinity.

Os mediators with these new ligands were synthesized using the same procedure used for Os free mediator. Their synthesis consists of two major process steps as outlined below. Details of these processing steps are described below.

The first process step involves the synthesis of Os intermediate, cis-bis(2,2'-bipyridyl)dichloroosmium(II), from commercially available osmium salt using the following scheme. The intermediate product is isolated through recrystallization in an ice bath.

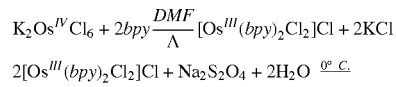

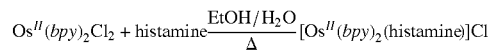

The second process step involves the reaction between Os intermediate and histamine or 4-imidazoleacetic acid (or a substituted bipyridine for preparation of the tris(bipyridyl) complexes) to produce Os mediators with the appropriate "handle". The desired product is then precipitated out from solution by addition of ammonium tetrafluoroborate.

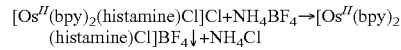

$[Os^{II}(bpy)_2(histamine)Cl]Cl+NH_4BF_4 \rightarrow [Os^{II}(bpy)_2(histamine)Cl]BF_4 \downarrow +NH_4Cl$ These Os mediators can also be easily converted to oxidized form, i.e. Os(III) using nitrosonium tetrafluoroborate. However, this is unnecessary since the Os revert back to reduced form anyway at alkaline conditions during conjugation reactions. And it does not require oxidized form of Os(III) for the detection on the biosensor.

A. Simple Mixed Mediator Measurement

1. Interdigitated array microelectrodes (IDA) are produced through photolithographic means by art-recognized methods, (See WO 97/34140; EP 0299,780; D. G. Sanderson and L B. Anderson, *Analytical Chemistry*, 57 (1985), 2388; Koichi Aoki et al., *J Electroanalytical Chemistry*, 256 91988) 269; and D. Niwa et la., *J Electroanalytical Chemistry*, 167 (1989) 291. Other means which are standard in lithographic processing may also be used to produce the desired patterns of a conductor on insulator substrate.

2. Reversible mediators are selected from those described herein and those described references (U.S. Pat. Nos.4,945, 045 and 5,589,325, the disclosures of which are incorporated herein by reference). Preferably two different mediators are selected with potentials which differ by at least 100 mV, more preferably at least 200 mV. Examples of suitable mediators include the Os(bipy)$_2$ImCl of this invention and in U.S. Pat. No. 5,589,326, the disclosure of which is incorporated herein by reference, and ferrocene, described in U.S. Pat. No. 4,945,045 and EP 0142301, the disclosures of which are incorporated herein by reference. Mixtures of these mediators are made in aqueous solution, for example phosphate-buffered saline (PBS). Concentrations between about 1 uM and 1000 uM may conveniently be measured.

3. The IDA is connected to a bipotentiostat, an instrument capable of controlling the potential of two separate electrodes. Also provided is a reference electrode. This non-polarizable electrode serves as the reference for the two applied potentials and may also serve as the counter electrode. Any non-polarizable electrode may be used, for example Ag/AgCl, such as may be obtained from ABI/Abtech. An auxiliary electrode can also be used for controlling current flow through the working electrodes. The mixtures are placed on the IDA electrode and the reference electrode also contacted with the mixture, or the IDA along with the reference electrode may be dipped into the mixture.

4. To measure Mediator 1 (Os(bipy)$_2$ImCl)

A cathodic potential is applied to one set of fingers of the IDA which is capable of reducing mediator 1 (ca −50 mV vs. Ag/AgCl). An anodic potential is applied to the other set of fingers of the IDA which is capable of oxidizing mediator 1 but not mediator 2 (or any other mediators) (ca 250 mV vs Ag/AgCl). After a short time (msec to sec), a steady state current will be measurable which is dependent only on the concentration of mediator 1.

5. To measure Mediator 2 (Ferrocene)

A cathodic potential is applied to one set of fingers of the IDA which is capable of reducing mediator 2 but not mediator 1 (ca 250 mV vs. Ag/AgCl). An anodic potential is applied to the other set of fingers of the IDA which is capable of oxidizing mediator 2 (ca 550 mV vs Ag/AgCl). After a short time (msec to sec), a steady state current will be measurable which is dependent only on the concentration of mediator 2.

Specific Binding Assay with Mixed Mediator Measurement.

Specific Assay of HbAlc in a blood sample

1. IDA electrodes are provided as in Paragraph A above.

2. Conjugates of mediators 1 and 2 and haptens or specific binding members are provided using art-recognized procedures for covalent coupling using either a homo-functional or hetero-functional linker. Specifically, a synthetic peptide corresponding to the N-terminal sequence of the β-chain of HbAlc is conjugated to the osmium complex. Similarly, a synthetic peptide corresponding to the N-terminal sequence of HbA0 is conjugated to a second mediator, for example ferrocene.

3. Antibodies for the analytes (HbAlc and HbA0) which react specifically with the N-terminal peptides which have been incorporated into the conjugate are provided by standard methods for producing polyclonal antibodies. In this case, sheep were immunized with carrier proteins to which were conjugated the synthetic peptide sequences for HbAlc and HbA0. Following the appropriate immunization schedule, the sheep were bled, and the antibody isolated from the blood via ion exchange chromatography, followed by immunosorbent purification on a column of the same N-terminal peptide with a different linker.

4. Appropriate stoichiometry of the reaction was determined for the two reactions independently by methods standard for immunoassay development. A solution containing a fixed amount of labeled conjugate was mixed with a solution with varying amounts of antibody, and, following an appropriate incubation period, the amount of free conjugate remaining was measured on the IDA electrode using the procedure described above. The amount of antibody just sufficient to achieve maximum inhibition of the conjugate (ca>80%) was selected.

5. Reagent solution 1 was made containing a mixture of the two conjugates in the appropriate concentrations. Reagent solution 2 was made containing a mixture of the two antibodies in the amounts determined above. A blood sample was diluted ca 20-fold in a solution of 25 mM citric acid/0.5% Brij-35. Following a 30 second incubation to allow for lysis and denaturation of the hemoglobin, to 66 uL of this diluted sample was added 33 uL of 1 M phosphate buffer, to adjust the pH back to neutral. 30 uL of antibody solution 2 was added, and the mixture allowed to incubate 30 sec. Then 30 uL of conjugate solution 1 was added, and the mixture measured on the IDA electrode. The concentration of HbAlc in the sample is related to the current measured from Mediator 1, and the concentration of HbA0 is related to the current from Mediator 2. The %HbAlc in the sample is related to the ratio of the measured amounts of Mediator 1 and Mediator 2.

Application to HbAlc Assay

Hemoglobin Alc is a specific glycohemoglobin in which the glycosylation takes place at the N-terminal of hemoglobin b-chain. The antibody binds specifically to HbAlc has an epitope sequence of Gluc-Val-His-Leu-Thr (SEQ ID NO:1). To facilitate conjugation to other molecules, a nonnative amino acid has been added to the sequence, e.g., Cys, Lys, or Lys-MH, to produce Alc peptides including: 1) Gluc-Val-His-Leu-Thr-Lys-MH (SEQ ID NO:2); 2) Gluc-Val-His-Leu-Tbr-Lys (SEQ ID NO:3); 2) Gluc-Val-His-Leu-Thr-Cys (SEQ ID NO:4).

HbAlc assay requires measuring both Alc concentration ahd total hemoglobin concentration and reports the results as a ratio of these two measurements (%HbAlc). It is advantageous to assay both Alc and total hemoglobin using same principle because ratioing would minimize biases due to environmental effects. Thus antibody has been raised to bind specifically to hemoglobins with unglycosylated N-terminus, i.e. with an epitope sequence of Val-His-Leu-Tbr (SEQ ID NO:5). Similarly, nonnative amino acid is added to the sequence to facilitate conjugation. The peptides used for total hemoglobin measurement is termed as A0 peptide. A0 peptides that have been used in the preparation of Os mediator-peptide conjugates include Val-His-Leu-Thr-Cys (SEQ ID NO:6) and Val-His-Leu-Thr-Lys (SEQ ID NO:7).

Conjugation Chemistry and Conjugates

There are many types of conjugation chemistry that can be employed to link Os mediator to a peptide. The following two conjugation chemistries employed for the preparation of Os mediator-peptide conjugates have also been commonly used for preparing protein conjugates: 1) formation of amide bond by reactive ester with primary amine; 2) formation of thioether bond by maleimide with sulfhydryl group. Amide bond is preferred over thioether bond because amide bond is generally more stable. Based the preferred conjugation chemistry, the ligand on Os mediator can be functionalized with either a primary amine group or a carboxylic acid group. The best location for these functional groups is believed to be the C-4 or C-5 positions on the imidazole ligand of Os mediator, however, functionalization through the non-Os-complexed imidazole ring nitrogen atom can also be carried out. Two different functionalized Os mediators were synthesized as described above.

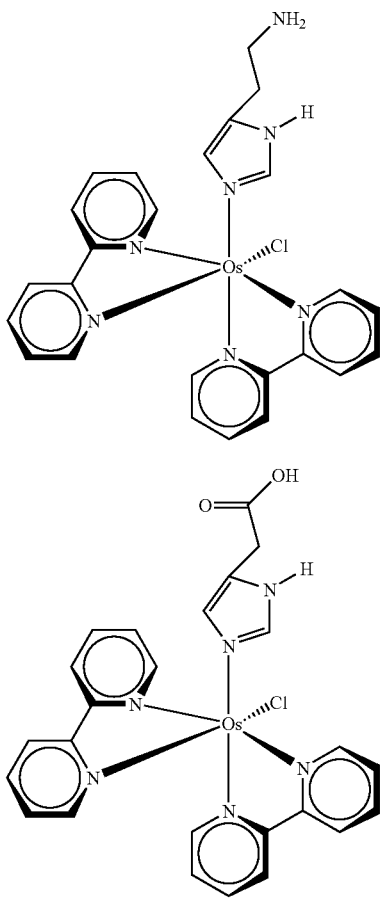

Os mediator (a) was formed with histamine while Os mediator (b) was formed with imidazolacetic acid. However, it was found that the imino nitrogen of the imidazole ring interferes with the activation of carboxylic acid group to reactive ester (i.e., N-hydroxysuccinimide ester) using carbodiimide. Thus, use of carboxylic acid functionalized Os mediator in the synthesis of Os mediator-peptide conjugates gave much less favorable results.

The amine group on histamine ligand of Os mediator readily reacts with N-hydroxysuccinimide (NHS) ester to form amide bond. Two types of crosslinkers have been employed to link Os mediator to peptides, (a) heterofunctional crosslinker, having a NHS ester at one end and the other end has a maleimide or a sulfhydryl group; and (b) homofunctional crosslinker, e.g. both ends have NHS esters.

In the case of heterofunctional crosslinker, the crosslinker is first reacted with Os mediator with histamine ligand (Os histamine) at 1:1 molar ratio. One particular point needs to be noted here. Os mediator in oxidized form, i.e. Os(III), can instantly oxidize sulfhydryl group to form disulfide bond. It is important to keep Os center in the reduced form by addition of a small amount of reductant such as sodium dithionite during the conjugation processes. The reaction progress can be monitored by analytical reverse-phase HPLC on a C18 column. Then the Os mediator-crosslinker adduct is isolated via preparative HPLC and the collected fraction is subsequently freeze-dried. Finally, the Os mediator-crosslinker adduct is reacted with the appropriate peptide to form Os mediator-peptide conjugate. Again, the product is isolated by collecting appropriate fraction in preparative HPLC and the collected fraction is then freeze-dried.

Two different heterofunctional crosslinkers have been used for the synthesis of Os mediator-peptide conjugates. SMCC (succinimidyl 4-[N-maleimidomethyl]cyclohexane-1-carboxylate) is used for cystein-containing peptide, while SATA (N-succinimidyl S-acetylthioacetate) is used for maleimide-containing peptide. Three Os mediator-peptide conjugates (two with A1c peptide and one with A0 peptide) have been made using heterofunctional crosslinkers and their structure are shown below: (a) Os-SMMC-A1c; (b) Os-SATA-A1c, and (c) Os-SATA-AO.

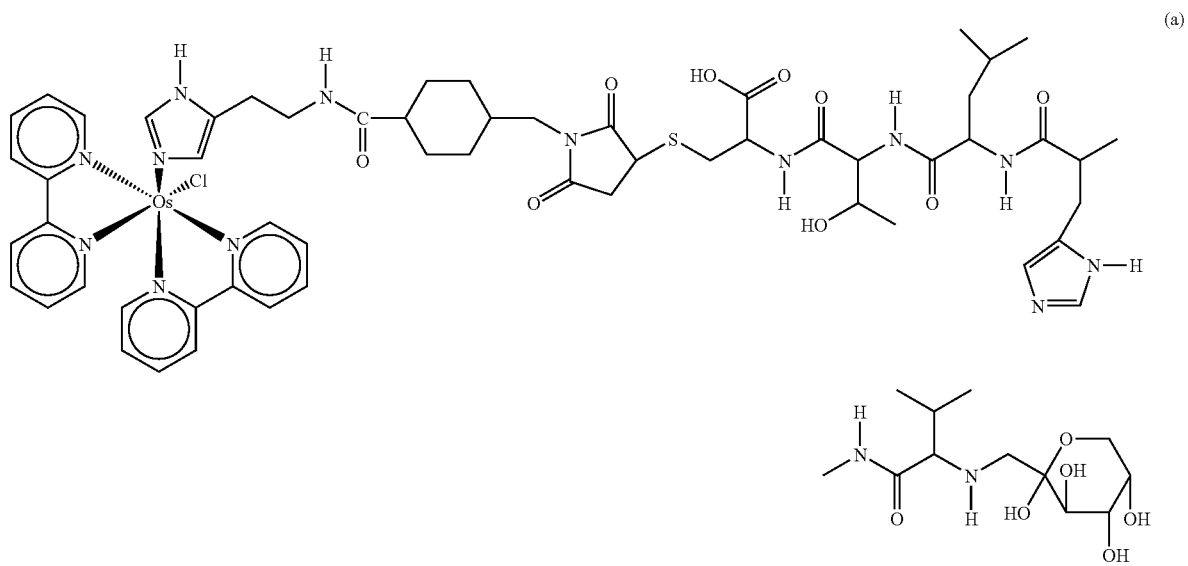

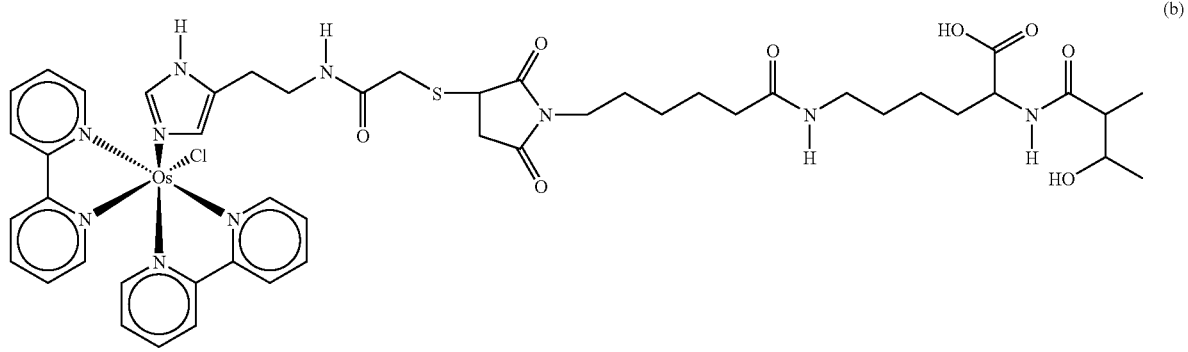

(b)

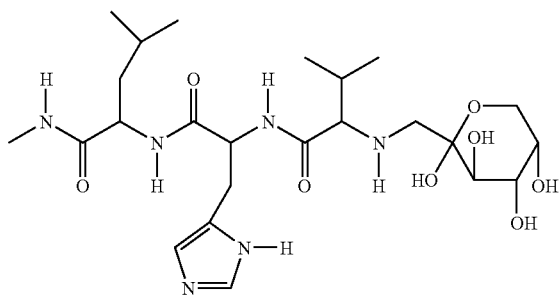

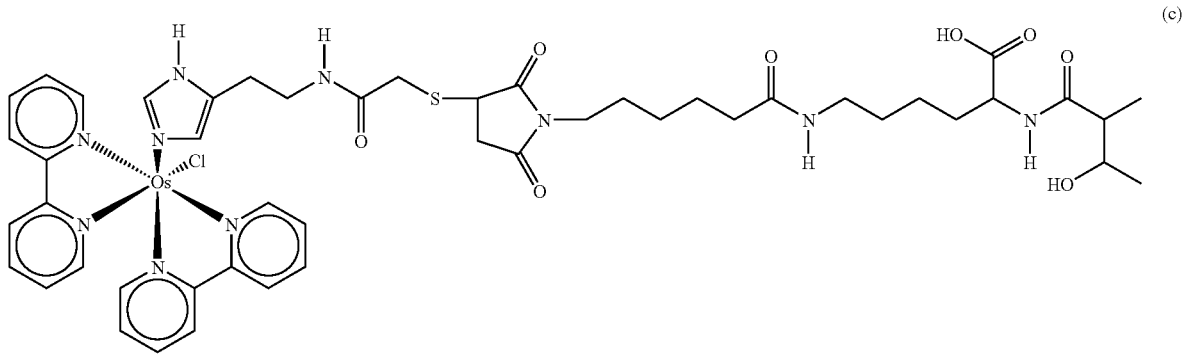

(c)

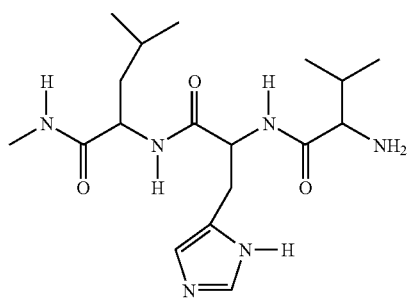

However, it has been found that these conjugates were not stable when they were stored as solutions. Analytical HPLC results indicated that these conjugates degrade. Mass spectroscopy confirmed that the instability is due to splitting of thioether bond present in these conjugates.

In order to avoid thioether bond in the conjugate, homofunctional crosslinker containing two NHS esters was used instead to prepare the conjugates. The crosslinker used was DSG (disuccinimidyl glutarate). In order to prevent the formation of crosslinked Os mediator, i.e. Os-crosslinker-Os, a large excess of homofunctional crosslinker was used in the reaction with Os histamine at 4:1 molar ratio. Under this condition, only the desired product, i.e. Os-crosslinker, was formed. The Os-DSG-Alc conjugate was similarly prepared using the procedure described earlier.

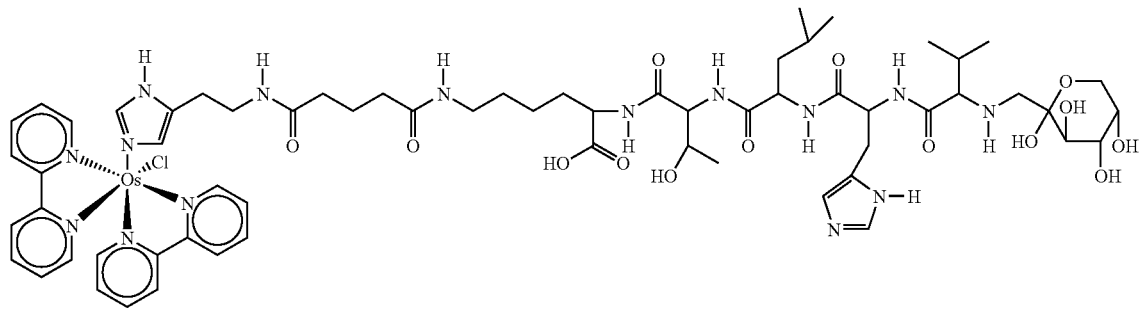

The preparation of analogous Os-DSG-A$_0$ conjugate requires and extra step since the unglycated N-terminal amine of HbA$_0$ peptide is also reactive toward NHS ester. In this case, the N-terminal amine of HbA$_0$ peptide is first protected by either a base-labile Fmoc[1] or an acid-labile Boc[2] group. After reacting with Os-DSG adduct to form Os-DSG-A$_0$ conjugate, the protecting group is then cleaved using appropriate deprotection method (adding base for Fmoc or acid for Boc). The peptides prepared by solid-phase peptide synthesis already have N-terminal Fmoc protecting groups. The protecting groups are usually removed prior to cleavage of peptide from the resin beads, but they can also be left on if so desired. The HbA$_0$ peptide from Zymed has an intact Fmoc protecting group at N-terminal. Using this strategy the Os-DSG-A$_0$ conjugate was successfully synthesized.

[1] Fmoc=9-flourenylmethyloxycarbonyl
[2] Boc=t-butyloxycarbonyl

Many analytes cannot be assayed using enzyme-based sensors. They require the development of affinity biosensors or immunosensors which are based on the selective binding of antigens to antibodies. The key to the detection of this binding event on electrochemical sensors is the inclusion of antigens labeled with redox labels. Bis(2,2'-bipyridyl) imidazolyl chloroosmium, a.k.a. Os mediator, possesses many properties that make it an excellent redox label for this purpose. In addition, a "handle" for linking it covalently to antigens can be added on without affecting its redox properties.

Several assay schemes can be used in affinity biosensors including, i) competitive binding assay (labeled antigen is competing for a limited number of binding sites); ii) sequential binding assays (labeled antigen is bound to excess binding sites); iii) heterogeneous assay (uses a separation step to separate bound and free labeled antigens); and iv) homogeneous assay (no separation step). The steps involved in a homogeneous sequential binding assay include binding the analyte to an antibody. The labeled antigen (analyte analog) binds to the remaining binding sites on the antibody. Finally the leftover free labeled antigen is detected at electrode surface. The resulting current will be a function of the amount of analyte present.

The detection of free labeled antigens can be achieved using either direct detection or amplified detection methods. Direct detection requires the use of advanced electrochemical techniques such as ac voltammetry, differential pulse voltammetry, square wave voltammetry or ac impedance in order to reach a sensitivity of 5 µM or less. Amplified detection methods use dc amperometry with amplification through reaction with enzyme or chemical reductants or by using interdigital array (IDA) microelectrodes. The preferred detection method is amplified amperometry through cycling of free Os mediator label by using IDA microelectrodes. However, amplified amperometry using Gluc-DOR enzyme can also be used. Fast mediation kinetics of Os mediator is very desirable because the magnitude of amplification is dependent on its mediation kinetic constant with the enzyme.

General Analytical HPLC Method for Osmium Conjugates

All HPLC analysis were performed using a Beckman System Gold HPLC system consists of a 126 pump module and a 168 diod array detector module. Stationary phase is a Vydac analytical reverse-phase C18 analytical column. Other parameters are listed below.

| Mobil Phase: | A = 0.1% TFA[3] in H$_2$O |
| --- | --- |
| | B = 0.1% TFA in CH$_3$CN |
| Flow rate: | 1 mL/min |
| Gradient: | 0–5 min: 10% B |
| | 5–45 min: 10% B –> 50% B at 1%/min |
| | 45–50 min: 100% B |
| Detector: | Channel A at 384 nm |
| | Channel B at 220 nm. |

Synthesis of Bis(2,2'-bipyridyl)dichloroosmium

1. Charge a 1 L one-neck RB flask with 19.335 grams K$_2$OsCl$_6$ (0.04019 mole) and 13.295 grams 2,2'-dipyridyl (0.08512 mole). Add 400 mL DMF to dissolve all reactants.
2. Heat the solution to reflux and then maintain reflux for 1 hour. Then turn off the heat and let solution cool to 30–40° C. at ambient.
3. Filter the reaction mixture using a medium grade glass-frit filter. Rinse the flask with additional 20 mL DMF and wash the filter.
4. Transfer the filtrate into a 3-L beaker. Charge another 2-L beaker with 22.799 grams of NaS204 and dissolve in 2 L deionized water. Add this solution to the beaker containing Os/DMF filtrate dropwise using a dropping funnel. Keep the solution stirring at all time.
5. Then cool the mixture in an ice bath for at least 3 hours. Add ice as necessary.
6. Filter the mixture "cold" using a ceramic filter with filter paper. Wash the content on the filter with 50 mL, water twice and 50 mL ether twice.
7. Dry the product under high vacuum at 50° C. overnight (at least 15 hours). Weigh the product and transfer into a brown bottle. Store in a desiccator at room temperature.

Typical yield=16 gram or 70%.

Product is analyzed by UV-Visible spectroscopy and elemental analysis.

| UV-Vis: | |
|---|---|
| Peak λ (nm) | ε ($M^{-1}cm^{-1}$) |
| 382 | 10,745 |
| 465 | 9,914 |
| 558 | 11,560 |
| 836 | 3,873 |

| EA: | | | | | | |
|---|---|---|---|---|---|---|
| | C % | H % | N % | Cl % | Os % | $H_2O$ % |
| Theoretical | 41.89 | 2.81 | 9.77 | 12.36 | 33.17 | 0 |
| Actual | 40.74 | 2.92 | 9.87 | 11.91 | | 0.41 |

Synthesis of Bis(2,2'-bipyridyl)histamine chloroosmium

1. Charge a 2 L one-neck RB flask with 11.3959 gram $Os(bpy)_2Cl_2$ (0.0198 mole) and 4.9836 gram histamine (0.0448 mole). Add 500 mL ethanol to dissolve the reactants. Then add 250 mL deionized water.
2. Heat the solution to reflux and maintain reflux for 6 hours. Let solution cool to RT at ambient.
3. Remove all ethanol using rotary evaporation. Then transfer the solution into a 500 mL beaker. Dissolve 2.136 gram $NH_4BF_4$ in 20 mL water. Add dropwise to Os solution. Precipitate forms. Cool in an ice bath for 30 min. Filter the mixture using a ceramic filter with filter paper. Wash the content on filter with ~20 mL water twice.
4. Dry under high vacuum at 50° C. overnight (at least 15 hour).
5. Weigh the product and transfer to a brown bottle. Store in a desiccator at room temperature.

Typical yield=7.6 gram or 52%.

Product is analyzed by UV-visible spectroscopy and HPLC.

| UV-Vis: | Peak λ (nm) | ε ($M^{-1}cm^{-1}$) |
|---|---|---|
| | 355 | 7,538 |
| | 424 | 7,334 |
| | 514 | 7,334 |
| | 722 | 2,775 |
| HPLC: | Elution time = 18.0 min | |
| | Purity by HPLC range from 65–85% | |

Preparation of [$Os(bpy)_2$(histamine)Cl]-heterofunctional Crosslinker Adduct

1. Weigh 0.1167 g [$Os(bpy)_2$(histamine)Cl]$BF_4$ (0.162 mmol) and transfer to a 5 mL Reacti-Vial. Add 1.0 mL DMF to dissolve the reactant. Add 25 μL triethylamine.
2. Add 0.0508 g SMCC(0.150 mmol) or 0.0390 g SATA (0.168 mmol). Stir the reactants at RT for 2 hours. Inject a sample into HPLC to monitor reaction progress.
3. If reaction is complete, dilute the solution with 0.1% TFA buffer to a final volume of 4.5 mL. Inject into preparative HPLC and collect the product peak.
4. Freeze dry the collected fraction overnight.
5. Weigh the product and transfer to a brown bottle. Store in a desiccated bag at −20° C.

Typical yield=40 mg or 25%.

Product is analyzed by HPLC and ES/MS.

| | HPLC | ES/MS |
|---|---|---|
| Os-SMCC: | Elution time = 32.1 min | $m^+/e$ = 434.2 |
| Os-SATA: | Elution time = 27.5 min | $m^+/e$ = 382.8 |

Preparation of [$Os(bpy)_2$(histamine)Cl]-homofunctional Crosslinker Adduct

1. Weigh 0.2042 g DSG (0.626 mmol) and transfer to a 5 mL Reacti-Vial. Add 0.75 mL DMF to dissolve the reactant.
2. Weigh 0.1023 g [$Os(bpy)_2$(histamine)Cl]$BF_4$ (0.142 mmol) and transfer to a separate 5 mL Reacti-Vial. Add 1.0 mL DMF to dissolve the reactant. Add 25 μL triethylamine. Then add Os/DMF solution dropwise to DSG/DW solution with constant stirring. After reacting for 2 hours at RT, inject a sample into HPLC to monitor reaction progress.
3. If reaction is complete, dilute the solution with 0.1% TFA buffer to a final volume of 4.5 mL. Inject into preparative HPLC and collect the product peak.
4. Freeze dry the collected fraction overnight.
5. Weigh the product and transfer to a brown bottle. Store in a desiccated bag at −20° C.

Typical yield=45 mg or 35%.

Product is analyzed by HPLC and ES/MS.

| | HPLC | ES/MS |
|---|---|---|
| Os-DSG: | Elution time = 27.1 min | $m^+/e$ = 429.2 and 859.6 |

Preparation of Os-SATA-Alc Conjugate

1. Weigh 40.5 mg Os-SATA (0.0529 mmol) and transfer to a 5 mL Reacti-Vial with stir bar. Add 1.0 mL PBS (pH 7.5) to dissolve. Add 20 mg $Na_2S_2O_4$ in order to keep Os in reduced form.
2. Add 1.0 mL deacetylation buffer (PBS pH7.5+0.5 M hydroxylamine and 25 mM EDTA) to deprotect the sulfhydryl group. Inject a sample into analytical HPLC to determine whether deprotection is complete by appearance of a new peak at 25.8 min.
3. Add 45 mg HbA1c-MH peptide (0.0474 mmol) and let react at RT for 1 hour. Inject a sample into analytical HPLC to monitor reaction progress.
4. If reaction is complete, dilute the mixture with 0.1% TFA buffer to a final volume of 4.5 mL. Inject into preparative HPLC to collect product peak.
5. Freeze dry the collected fraction overnight (at least 15 hour).
6. Weigh the product and transfer to a brown bottle. Store in a desiccated bag at −20° C.

Typical yield=12 mg

Product is analyzed by HPLC and ES/MS.

|  | HPLC | ES/MS |
|---|---|---|
| Os-SATA-Alc: | elution time = 27.6 min | m$^+$/e = 559.1 and 838.5 |

Preparation of Os-SMCC-Alc Conjugate
1. Weigh 39.0 mg Os-SMCC (0.0452 mmol) and transfer to a 5 mL Reacti-Vial with stir bar. Add 1.0 mL PBS (pH 6.0) to dissolve.
2. Add 30.0 mg Hblc-Cys peptide (0.0450 mmol). Let reaction proceed at RT for 2 hours. Inject a sample into analytical HPLC to monitor reaction progress.
3. If reaction is complete, dilute the mixture with 0.1% TFA buffer to a final volume of 4.5 mL. Inject into preparative HPLC to collect product peak.
4. Freeze dry the collected fraction overnight (at least 15 hour).
5. Weigh the product and transfer to a brown bottle. Store in a desiccated bag at −20° C.

Typical yield=12 mg

Product is analyzed by HPLC and ES/MS.

|  | HPLC | ES/MS |
|---|---|---|
| Os-SMCC-Alc: | elution time = 27.6 min | m$^+$/e = 480.5 and 534.4 |

Preparation of Os-SMCC-Ao Conjugate
1. Weigh 37.0 mg Os-SMCC (0.0426 mmol) and transfer to a 5 mL Reacti-Vial with stir bar. Add 1.0 mL PBS (pH=6.0) to dissolve.
2. Add 24.3 mg HbAo-Cys peptide (0.0425 mmol). Let reaction proceed at RT for 2 hours. Inject a sample into analytical HPLC to monitor reaction progress.
3. If reaction is complete, dilute the mixture with 0.1% TFA buffer to a final volume of 4.5 mL. Inject into preparative HPLC and collect the product peak.
4. Freeze dry the collected fraction overnight (at least 15 hour).
5. Weigh the product and transfer to a brown bottle. Store in a desiccated bag at −20° C.

Typical yield=15 mg

Product is analyzed by HPLC and ES/MS.

|  | HPLC | ES/MS |
|---|---|---|
| Os-SMCC-A$_o$°: | elution time = 27.9 min | m$^+$/e = 360.7 and 720.5 |

Preparation of Os-DSG-Alc Conjugate
1. Weigh 32.0 mg Os-DSG (0.037 mmol) and transfer to a 5 mL Reacti-Vial with stir bar. Add 0.75 mL DMF to dissolve. Add 25 µL triethylamine.
2. Add 26.5 mg HbAlc-Lys peptide (0.0349 mmol). Let reaction proceed at RT for 2 hours. Inject a sample into analytical BPLC to monitor reaction progress.
3. If reaction is complete, dilute the mixture with 0.1% TFA buffer to a final volume of 4.5 mL. Inject into preparative HPLC and collect the product peak.
4. Freeze dry the collected fraction overnight (at least 15 hour).
5. Weigh the product and transfer to a brown bottle. Store in a desiccated bag at −20° C.

Typical yield=16 mg

Product is analyzed by HPLC and ES/MS.

|  | HPLC | ES/MS |
|---|---|---|
| Os-DSG-Alc: | elution time = 23.5 min | m$^+$/e = 501.8 and 752.8 |

Preparation of Os-DSG-Ao Conjugate
1. Weigh 52.0 mg Os-DSG (0.0605 mmol) and transfer to a 5 mL Reacti-Vial with stir bar. Add 1.0 mL DMF to dissolve. Add 25 µL triethylamine.
2. Add 49.1 mg Fmoc-HbA$_0$ peptide (0.0606 mmol). Let reaction proceed at RT for 2 hours. Inject a sample into analytical HPLC to monitor reaction progress by the appearance of peak at 40.3 min for Os-DSG-A$_0$(Fmoc).
3. If reaction is complete, inject additional 100 µL triethylamine. After 1 hour, inject sample into analytical HPLC to determine whether all Fmoc protection group is removed by disappearance of the peak at 40.3 min.
4. If removal of Fmoc is complete, dilute the mixture with 0.1% TFA buffer to a final volume of 4.5 mL. Inject into preparative HPLC to collect product peak.
5. Freeze dry the collected fraction overnight (at least 15 hour).
6. Weigh the product and transfer to a brown bottle. Store in a desiccated bag at −20° C.

Typical yield=16 mg

Product is analyzed by HPLC and ES/MS.

|  | HPLC | ES/MS |
|---|---|---|
| Os-DSG-A$_o$: | elution time = 23.2 min | m$^+$/e = 447.4 and 670.3 |

Synthesis of bis(4,4'-dimethyl-2,2'-bipyridyl) 4-methyl-4'-carboxylpropyl-2,2'-bipyridyl osmium [Os(dm-bpy)2(mcp-bpy)]Cl2

Potassium hexachloroosmium was reacted with 4,4'-dimethyl-2,2'-dipyridyl at 1:2 molar ratio by refluxing in DMF. The potassium chloride precipitate was filtered and the dimethyl-bipyridyl dichloroosmium complex was reduced from +3 oxidation state to +2 oxidation state using excess sodium dithionite. The product was recrystallized in DMF/water mixture at 0° and recovered by filtration.

4,4'-Dimethyl-2,2'-bipyridyl dichloroosmium was reacted with 4-methyl-4'-carboxylpropyl-2,2'-dipyridyl by refluxing in ethylene glycol. The solvent was removed by rotary evaporation. The product was dissolved in DMF and precipitate in ethyl ether. The product was dried in a vacuum oven overnight.

Analyticals: Product and intermediate product were analyzed by HPLC and mass spectroscopy for purity and identity of the compound.

Os(dm-bpy)2Cl2: Theoretical MW=629.6, MS showed 8 isotope peaks with most abundant peak at 630. HLPC elution time at 29.94 min with a purity of 90%+

Os(dm-bpy)2(mcp-bpy): MS confirmed the MW at 814.5 and HPLC showed a purity greater than 85%.

Synthesis of biotin-Os Complex Conjugate
Biotin-Os(dm-bpy)2(mcp-bpy)Cl2

The carboxyl group was activated by reacting the above Os complex with dicyclohexylcarbodiimide in the presence of N-hydroxysuccinimide. The active ester Os complex was isolated using preparative HPLC method and then reacted with amine-containing biotin to form the final conjugate.

Experiment to Independently Measure the Concentration of Two Electroactive Conjugate Species Os(bipy)HisCl-DSG-HbAlc was prepared as described above.

Ferrocene-AMCHA-DADOO-biotin was prepared from ferrocene monocarboxylic acid, the crosslinker aminomethylcyclohexylic acid, the chain extender 1,8-diamino-3,6-DiOxoOctane and biotin as described elsewhere.

Mixtures of the two conjugates were prepared to evaluate the ability of the method of the invention to independently measure the concentration of the conjugates, and make corrections for variations in reagent amounts, electrode response, and environmental conditions.

Part 1: Simple Mixed Conjugate Response

The following matrix of solutions was prepared in 10 mM phosphate buffer with 150 mM NaCl and 0.5% Brij-35, a non-ionic surfactant.

| Os-DSG-HbAlc uM/l | Ferrocene-Biotin uM/l | Os-DSG-HbAlc uM/l | Ferrocene-Biotin uM/l |
|---|---|---|---|
| 0 | 0 | 0 | 12.5 |
| 6.25 | 0 | 6.25 | 12.5 |
| 12.5 | 0 | 12.5 | 12.5 |
| 25 | 0 | 25 | 12.5 |

| Os-DSG-HbAlc uM/l | Ferrocene-Biotin uM/l | Os-DSG-HbAlc uM/l | Ferrocene-Biotin uM/l |
|---|---|---|---|
| 0 | 25 | 0 | 50 |
| 6.25 | 25 | 6.25 | 50 |
| 12.5 | 25 | 12.5 | 50 |
| 25 | 25 | 25 | 50 |

An Interdigitated array (IDA) microelectrode was fabricated according to the procedures described. In addition to the IDA, the chip had a silver/silver chloride electrode on the surface to function as the reference electrode and counter electrode. This electrode was produced with the same lithographic process, and then electroplated with silver and silver chloride according to standard techniques. The IDA was connected to a bipotentiostat capable of controlling the potential relative to the reference and measuring the current at each of the electrodes of the IDA. Aliquots of the solutions were placed onto the surface of the chip, such that the IDA and the reference electrodes were covered.

Figure 9:
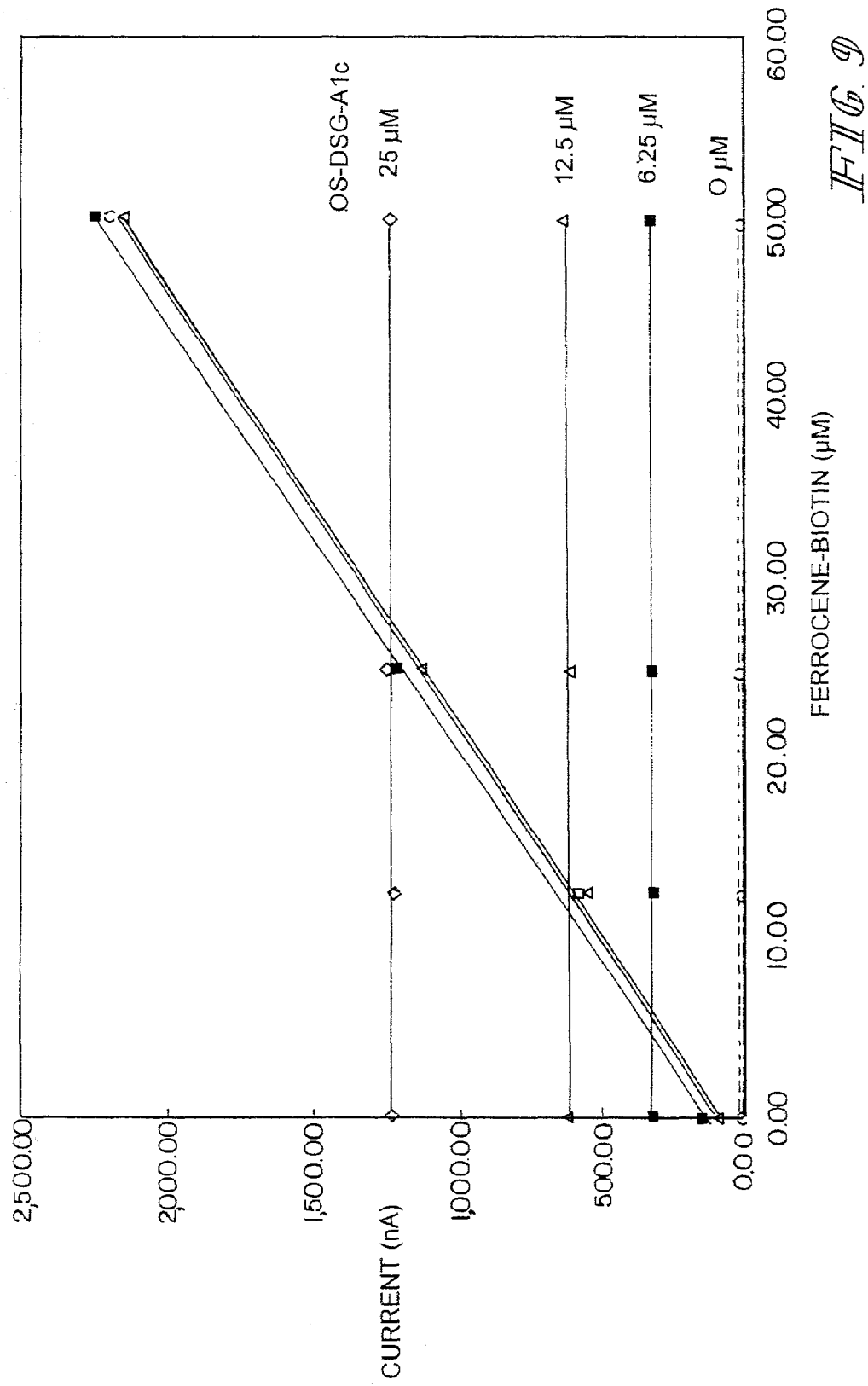
FIG. 9 is a graphic presentation of current flow vs. concentration of a ferrocene-biotin conjugate in the presence of varying amounts of an osmium complex conjugate on interdigitated array electrodes with bipotentiostatic control.

Measurements were made by first applying −100 mV (vs. Ag/AgCl) to one electrode of the IDA, and 200 mV to the other electrode for a period of 30 seconds. At this time, current was measured at each electrode. Then 200 mV was applied to one electrode, and 550 mV to the other. After 30 seconds, current was again measured. See FIG. 9 for a summary of the results, which clearly demonstrate that the concentrations of the two mediators can be independently measured with this method.

Part 2. Concentration Co-variance of Dual Mediators on IDA Electrodes

In this experiment, it was demonstrated that by making a mixture of known concentrations of two different mediators, and measuring different dilutions of that mixture by the method of the invention, the ratio of the concentrations of the mediators remains constant. (Internal standard application).

The same two mediator conjugates were used as in Part 1. (Os-DSG-Alc and Fc-Bi)

From a solution containing 40 uM of each conjugate, solutions containing 27 uM, 32 uM, and 36 uM of each conjugate were prepared in the same buffer (PBS/Brij).

The solutions were measured as in the previous example. Each solution was measured on 5 different IDA electrodes. The results are presented as the means, standard deviations, and coefficient of variation for each solution separately, and for all solutions pooled over all electrodes.

| Individual concentrations | | Os-DSG-Alc | Fc-Bi | Os/FC |
|---|---|---|---|---|
| 28 uM | Mean | 156 | 85 | 1.84 |
| | S.D. | 17.5 | 13.2 | 0.08 |
| | % C.V. | 11.2 | 15.5 | 4.4 |
| 32 uM | Mean | 165 | 88 | 1.88 |
| | S.D. | 11 | 7.2 | 0.04 |
| | % C.V. | 6.7 | 8.2 | 2.0 |
| 36 uM | Mean | 189 | 102 | 1.85 |
| | S.D. | 12.5 | 6.9 | 0.04 |
| | % C.V. | 6.6 | 6.7 | 2.3 |
| 40 uM | Mean | 208 | 110 | 1.90 |
| | S.D. | 9.5 | 5.5 | 0.06 |
| | % C.V. | 4.6 | 5.0 | 3.4 |
| Pooled Concentrations | Mean | 182 | 97 | 1.87 |
| | S.D. | 24.4 | 13.2 | 0.06 |
| | % C.V. | 13.4 | 13.5 | 3.4 |

This example clearly demonstrates that the internal standard effect of measuring two conjugates or mediators and calculating the ratio gives significantly improved precision of measurement, not only within each solution (compensation for variation between electrodes) but over all solutions (compensation for variation in sample dilution or amount).

Part 3. Temperature Compensation

It was desired to show the effectiveness of the method in compensating for environmental influences such as Temperature variation on the accuracy or the measurement.

The same two conjugates were prepared in solution at 40 uM as before. They were measured as before on IDA electrodes, either at room temperature or warmed to 35–40 C. on a heated metal plate prior to the measurement. The solutions were also warmed to 37 C. prior to application to the electrodes.

|  | Room Temperature (23 C.) | Warmed (35–40) C. | Ratio of response Warm/RT |
| --- | --- | --- | --- |
| Os-DSG-A1c | 261 | 387 | 1.45 |
| Fc-Bi | 179 | 268 | 1.5 |
| Ratio Os/Fc | 1.46 | 1.44 | 0.99 |

As demonstrated by the results, the measured values increase by almost 50% in the case of the warmed samples, which would lead to a large measurement error. However the use of the internal standard and ratio calculation effectively eliminates the temperature dependence of the result.

Immunoassay Detection of HbA1c with Osmium Mediator Conjugates

The goal of all diabetic therapy is to maintain a near normal level of glucose in the blood. Home blood glucose kits are available to monitor the current glucose values and are valuable for diabetics to adjust day to day insulin doses and eating habits. Unfortunately, since the tests only measures a point in time result, it does not tell them the overall effectiveness of their actions in maintaining glycemic control. Measurement of glycosylated hemoglobin is now becoming widely accepted as an index of mean blood glucose concentrations over the preceding 6–8 weeks and thus provides a measure of the effectiveness of a diabetic's total therapy during periods of stable control. Since monitoring a diabetic's glycated hemoglobin can lead to improved glycemic control, the ADA recommends routine measurements of four times a year up to once a month for less stable type I diabetics.

Several technologies are available for the measurement of glycated hemoglobin. They include immunoassays for HbA1c (TinaQuant, BMC; DCA2000, Ames; and Unimate, Roche), ion exchange (Variant, BioRad; Eagle Diagnostics), and affinity chromatography (ColumnMate, Helena; GlyHb, Pierce).

One objective of this project is to develop a simple to use disposable strip for electrochemical detection of HbA1c for use in both physician offices and the home.

The most significant parameter for assessing patient condition is ratio of HbA1c to $HbA_0$, and thus the measurement of both glycated (HbA1c) and nonglycated (HbA0) values is required to calculate the ratio. This requires two separate measurements. It is preferable to use the same technology to measure both the glycated and nonglycated fractions, thus removing some sample and environmental interferences.

Measurement of HbA1c via electrochemical immunoassay is described below. Electrochemical HbA0 immunoassay measurements are carried out using the same methods as that for HbA1c. The concentrations of $HbA_0$ are significantly higher. One alternative to $A_0$ measurements using immunoaffinity would be to measure total hemoglobin directly using biamperometry or differential pulse voltammetry. This can be easily accomplished since hemoglobin is readily oxidized by $[Os(bpy)_2(im)Cl]^{2+}Cl_2$.

The N-terminal valine of the β-chain of hemoglobin A is the site of glycosylation in HbA1c, and serves as a recognition site for the antibody. In whole blood the N-terminal valine is not accessible for the antibody to bind. Access is gained by lysing the red cells to release the hemoglobin followed by a conformation change (denaturing or unraveling) to adequately expose the HbA1c epitope. Dilution of the sample may occur as part of the lysing/denaturing process or may be required post denaturing to prepare the sample for the antibody (adjust pH, other) or bring the sample into a range suitable for electrochemical immunoassay. In one embodiment, a fixed amount of antibody is incubated with the prepared sample and it binds to the HbA1c epitopes of the sample. The free antibody and the antibody bound sample is then combined with the osmium peptide conjugate (A1c or $A_0$) to allow the remaining unbound antibody to bind to the mediator label. When the mediator is bound to the antibody (a macromolecule), it can not freely diffuse to interact with the electrode and thus currents generated are significantly reduced. The remaining unbound mediator label is therefore proportional to the concentration of HbA1c in the sample. The unbound mediator can be measured electrochemically either through an enzyme amplification method or directly using an interdigitated array electrode with bipotentiostatic control.

Figure 4:
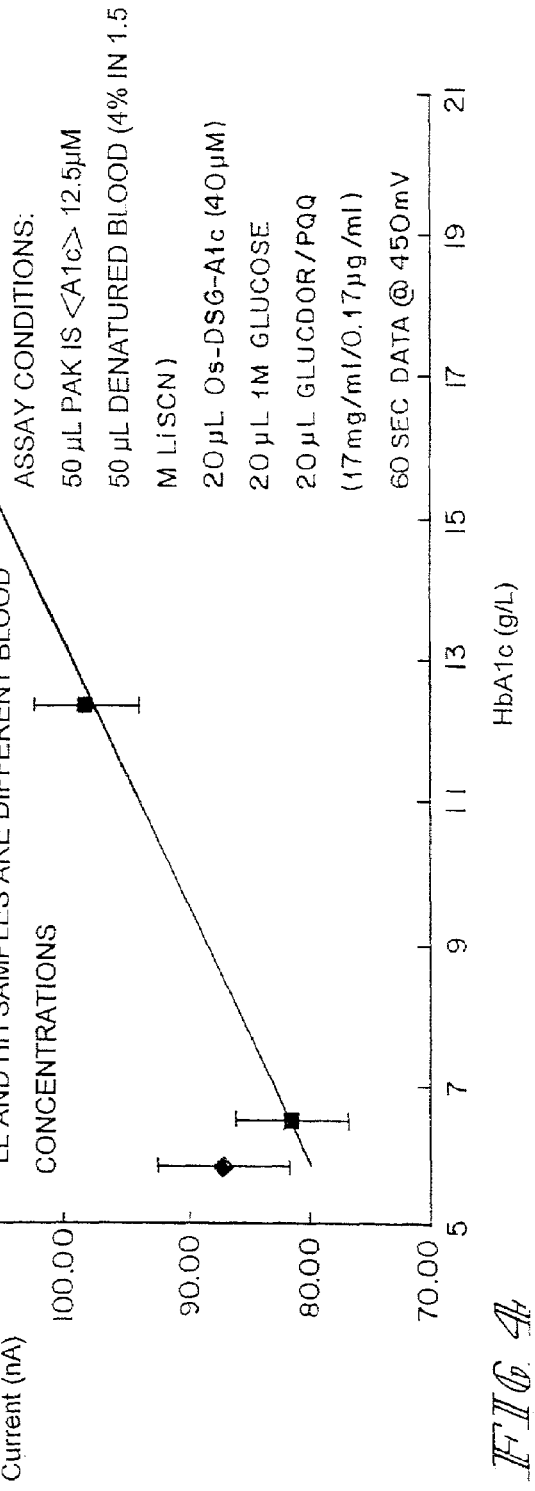
FIG. 4 is a graphic illustration of current flow vs. concentration of glycosylated hemoglobin (HbAlc) in blood samples using an osmium conjugate and enzyme amplified DC amperometry.

An electrochemical HbA1c immunoassay response was demonstrated on gold electrodes using enzyme amplification in a biamperometric mode. The experimental conditions were not thoroughly optimized and the assay components were premixed in microcentrifuge tubes and then pipette onto the gold 4.95 mm² E-cells. The experimental conditions for this assay are shown in Table 1. Table 2 shows the dose response data for the low, medium, and high HbA1c samples. FIG. 4 shows the dose response with two additional points LL and HH which represent a diluted low and a concentrated high sample. The higher currents for LL may possibly be explained by a reduction in blood proteins (due to dilution) leading to a reduction in electrode fouling.

TABLE 1

Dose Response Conditions

| Sample Preparation (denaturing) | Reagents | Electrochemical Measurement |
| --- | --- | --- |
| 1. 20 µL Lysed blood for L, M, H samples (previously frozen whole blood<br>2. 18 µL of L (LL) and 22 µL of H for (HH)<br>3. 480 µL 1.5 M LiSCN with 0.1% Tween<br>4. Mix and allow to denature for 10 minutes (Vortex) | 1. 50 µL 12.5 µM PAB IS<A1c>in PBST<br>2. 50 µL denatured Blood<br>3. 20 µL 40 µM Os-DSG-A1c in DI $H_2O$<br>4. 20 µL 1M Glucose in DI $H_2O$<br>5. 20 µL Glucdor/PQQ (1.7 mg/ml/0.17 mg/ml) | 1. VXI Waveform E-450 mV for 60s<br>2. Insert Gold Electrodes WE = 1.5 × 3.3 mm<br>3. Apply 20 µL Reagent<br>4. Start biamperometric measurement mode<br>5. Extract 60 sec data |

TABLE 2

Blood Dose Response Data

| g/L | #1 | #2 | #3 | #4 | Separate denaturant step Mean | SD | CV | All Data Mean | SD | CV |
|---|---|---|---|---|---|---|---|---|---|---|
| Current @ 60 seconds (nA) | | | | | | | | | | |
| 6.49 | 76.28 | 78.34 | 84.79 | 78.47 | 79.47 | 3.69 | 4.64 | 81.54 | 4.67 | 5.73 |
| 6.49 | 80.30 | 82.97 | 86.82 | 83.48 | 83.48 | 2.69 | 3.22 | | | |
| 6.49 | 83.25 | 85.49 | 90.05 | 86.67 | 86.67 | 2.94 | 3.40 | | | |
| 6.49 | 76.66 | 71.72 | 78.24 | 76.56 | 76.55 | 1.44 | 1.88 | | | |
| 12.34 | 95.61 | 95.05 | 93.06 | 94.02 | 94.44 | 1.13 | 1.20 | 98.31 | 4.19 | 4.26 |
| 12.34 | 98.59 | 106.29 | 103.81 | 102.08 | 102.08 | 3.60 | 3.53 | | | |
| 12.34 | 95.80 | 103.14 | 99.90 | 99.32 | 99.32 | 3.06 | 3.08 | | | |
| 12.34 | 93.16 | 96.2 | 103.10 | 97.41 | 97.41 | 4.16 | 4.27 | | | |
| 18.20 | 100.06 | 110.83 | 119.08 | 112.52 | 112.52 | 9.29 | 8.26 | 113.48 | 5.08 | 4.48 |
| 18.20 | 115.43 | 116.93 | 116.77 | 116.26 | 116.26 | 0.71 | 0.61 | | | |
| 18.20 | 116.12 | 109.72 | 112.07 | 112.21 | 112.21 | 2.78 | 2.48 | | | |
| 18.20 | 118.13 | 112.16 | 109.8 | 112.93 | 112.93 | 3.61 | 3.20 | | | |
| Calculated HbA1c (g/dL) | | | | | | | | | | |
| 6.49 | 4.46 | 5.22 | 7.58 | 5.26 | 5.63 | 1.35 | 24.00 | 6.39 | 1.71 | 26.80 |
| 6.49 | 5.94 | 6.91 | 8.33 | 7.23 | 7.10 | 0.99 | 13.87 | | | |
| 6.49 | 7.02 | 7.84 | 9.51 | 8.72 | 8.27 | 1.08 | 13.05 | | | |
| 6.49 | 4.60 | 3.89 | 5.18 | 4.56 | 4.56 | 0.53 | 11.58 | | | |
| 12.34 | 11.55 | 11.34 | 10.61 | 10.97 | 11.12 | 0.41 | .3.72 | 12.54 | 1.54 | 12.25 |
| 12.34 | 12.64 | 15.46 | 14.56 | 13.03 | 13.92 | 1.32 | 9.48 | | | |
| 12.34 | 11.62 | 14.31 | 13.12 | 12.58 | 12.91 | 1.12 | 8.70 | | | |
| 12.34 | 10.65 | 11.77 | 14.29 | 12.12 | 12.21 | 1.53 | 12.50 | | | |
| 18.20 | 13.18 | 17.13 | 20.15 | 20.54 | 17.75 | 3.41 | 19.19 | 18.10 | 1.86 | 10.29 |
| 18.20 | 18.82 | 19.37 | 19.31 | 19.00 | 19.12 | 0.26 | 1.36 | | | |
| 18.20 | 19.07 | 16.72 | 17.58 | 17.16 | 17.63 | 1.02 | 5.78 | | | |
| 18.20 | 19.81 | 17.62 | 16.75 | 17.42 | 147.90 | 1.32 | 7.40 | | | | n = 16, 4 denaturation for each HbA1c sample × 4 replicates each, Y = 2.82 × + 62.54, See fie 4435051 A.xls Blood lysis is necessary to release the hemoglobin followed by denaturing to expose the HbA1c epitope. Lysis can easily be accomplished via surfactants, osmotic effects of dilution with water, and directly by many denaturants. Blood lysed through a freeze/thaw cycle was shown not to significantly interfere with the biamperometric measurement ("open rate" with and without lysed blood was almost identical). Conversely, denaturing the lysed blood with a variety of known denaturants to expose the HbA1c epitope has shown significant suppression of the electrochemical response, inhibiting measurement of an HbA1c dose response. Only LiSCN and citric acid from the list of evaluated denaturants shown in Table 3 was able to expose the A1c epitope and minimize protein fouling enough to measure an HbA1c dose response.

Denaturing the sample for antibody recognition without severely fouling the electrode surface is important for successful development of an HbA1c immunoassay. Although LiSCN has been used almost exclusively to show feasibility, it has many limitations that would hinder its use in the disposable. Citric acid, a solid at RT may offer benefits as a denaturant if it could be dried onto a strip followed by a diluent to adjust the pH to neutral. Acid or base blood denaturing followed by a final pH adjustment with a buffered diluent is an area worth further evaluation. One problem that was initially encountered was precipitation in adjusting the pH back to neutral, which can be overcome by using a different buffer or with the addition of surfactants.

TABLE 3

Blood Denaturants

Figure 5:
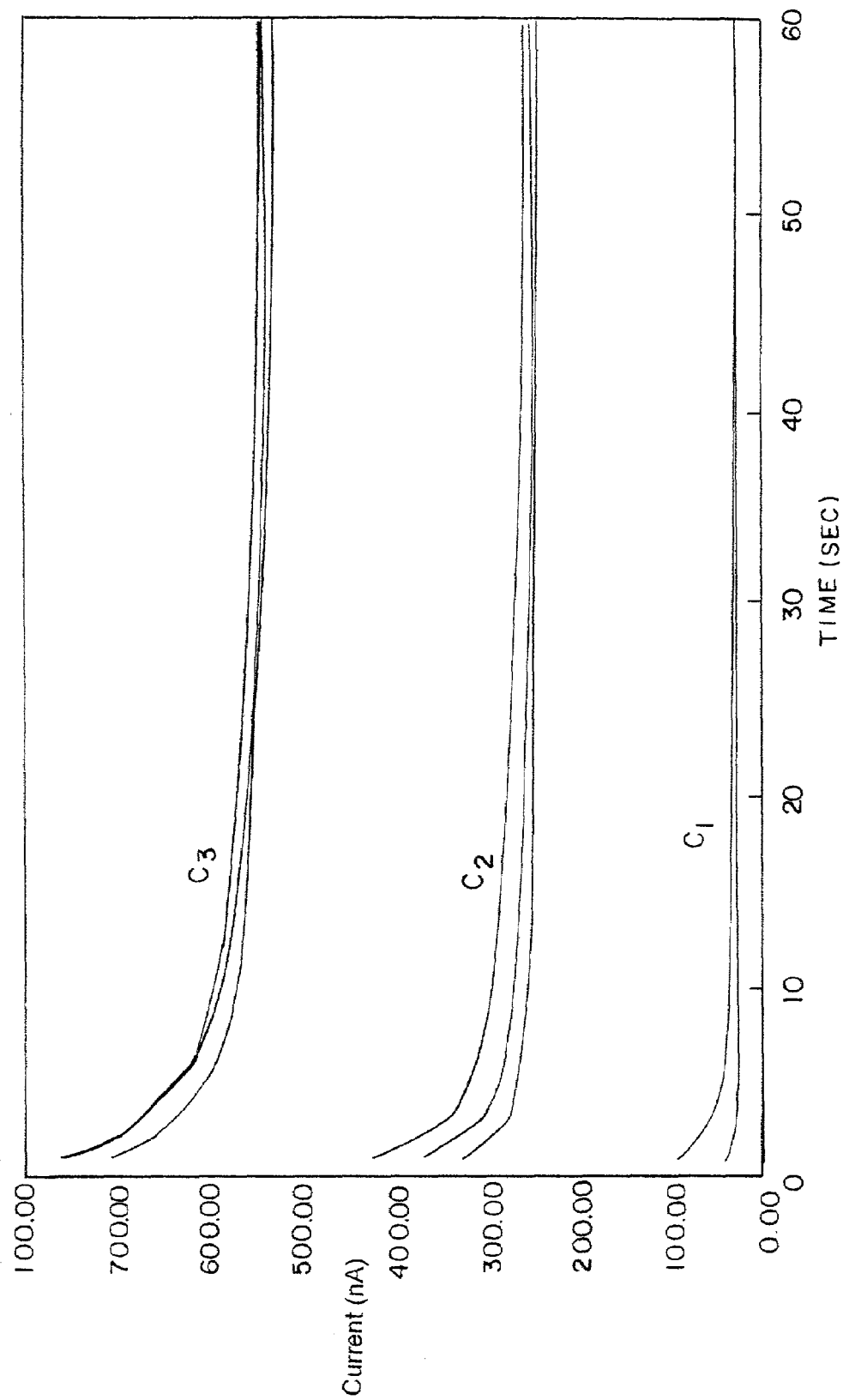
FIG. 5 is a graphic illustration of the inhibition of current flow due to free conjugate as a function of antibody concentration (Cn) as measured using enzyme amplified DC amperometry [$C_1, > C_2, > C_3$].

| Method | Comments |
|---|---|
| KSCN | Initial work did not show a dose response with KSCN denatured blood. |
| | KSCN has a larger negative effect on the electrochemical response than LiSCN. |
| | Literature shows that LiSCN is more effective than KSCN (concentrated efforts on LiSCN). |
| DCA2000 Buffer | Denaturing of blood not evident with the higher blood concentrations required for this assay. Higher concentrations of LiSCN are shown below. |
| LiSCN | Method used by Ames DCA2000 HbA1c immunoassay. |
| Citric, Sulfuric, Hydrochloric, & Perchloric Acid | Blood HbA1c dose response (high/low) was seen with citric acid and was comparable to the response with LiSCN |
| | Evidence of blood denaturing was seen by all: "solution turned brown." Citric acid is preferred. |
| | Adjustment of pH to neutral after denaturing also saw problems of precipitation. Enzyme mediated responses with Gluc-Dor at pH 5.7 reduces response 50% compared to pH 7–8. |
| | Citric acid blood denaturing method is shown in FIG. 5. |
| Pepsin/Citric Acid | Roche HbA1c immunoassay uses pepsin/citric acid to hemolyze and proteolytically degrade hemoglobin to glycoproteins accessible by the antibody. |
| | Denaturation was apparent by the color change to a brownish red solution. |
| | Hemoglobin A1c dose response (high/low) was obtained comparable to LiSCN and citric acid denaturants. The procedure was identical to that of citric acid used above with the exception of pepsin added to the acid. Results were identical to that of citric acid. |

TABLE 3-continued

Blood Denaturants

| Method | Comments |
| --- | --- |
| TTAB (Tetra decyltrimethyl ammonium bromide) | Method of denaturing used in the TinaQuant HbAlc turbidimetric immunoassay.<br>Evidence of denaturing: "solution turned green"<br>TTAB concentrations 0.0125–0.2% severely suppressed enzyme mediated (Glucdor/PQQ/Glucose) biamperometric measurements. Open rates were 16–50 nA compared to 140 nA without TTAB. |
| NaOH | Evidence of denaturing: "solution turned brown."<br>NaOH does not adversely effect the enzyme mediated electrochemistry. Even at high pH the open rates do not change, although pH adjustment will probably be required to bring it within an optimal range for the antibody.<br>NaOH denatured blood suppresses the open rates probably due to protein fouling.<br>Lowering the pH to neutral tends to cause some precipitation. |

Electrode fouling caused by denatured blood proteins adsorbing to the electrode surface can impede electron transfer and thus decrease electrode sensitivity. Electrode fouling or passivation occurs more or less immediately following sample contact with the surface thus minimizing the severity of denaturing in the sample should be the first approach. Surface conditions that are hydrophobic will favor adhesion of the proteins and thus fouling may be minimized with electrode surfaces of higher surface energies. This explains why gold electrodes shows less fouling with denatured blood than palladium. Reduction of protein fouling may be achieved by changing or protecting the electrode surface. Modifications that make the surface more hydrophilic should reduce the amount of fouling and can be accomplished by argon or oxygen plasma treatment or corona treatment. Selective coatings that could block the proteins from reaching the electrode surface can usually partially circumvent the problem have been used in the field to reduce fouling. Unfortunately, dramatic decreases in responses greater than seen with the denatured blood proteins are normally noted with their use. Hydrophilic coatings such as PEO were also evaluated and showed some improvement, but have similar problems of decreased magnitude and precision caused by forcing reagents to diffuse through the polymers. Reagents dispensed and dried over the electrodes may help reduce the magnitude of protein fouling with less negative effects.

TABLE 4

Effective Blood Denaturing Procedure for 2% Blood

| LiSCN (One Step) | LiSCN (Two Step) | Citric Acid (2 Step) |
| --- | --- | --- |
| 40 µL 6M LiSCN<br>20 µL 5% Tween in PBS<br>20 µL Blood<br>Mix (vortex) and allow to denature for 10 minutes. Dilute with 920 µL DI H₂O. | 960 µL 1.5M LiSCN<br>20 µL 5% Tween in PBS<br>20 µL Blood<br>Mix (vortex) and allow to denature for 10 minutes. | 200 µL 0.2M Citric Acid<br>20 µL 5% Tween in PBS<br>20 µL Blood<br>Mix (vortex) and allow to denature for 10 minutes. Dilute with 760 µL 8X PBS (0.1% Tween) |
| Denaturing time was not optimized. Limited data supports longer times for better precision using this method. | Denaturing time was not optimized. Data indicates shorter times may be adequate. | No optimization studies were performed. |

PBS = 10 mM Phosphate Buffer, 2.7 mM KCl, 137 mM NaCl pH = 7.4
Increased level of surfactant (5% Tween) reduces or eliminates precipitate.

Mediator concentration dose response, inhibition with antibody and reversal with a BSA-Alc polyhaptan were evaluated and summarized in Table 5. The Os-DSG-Alc is stable in a lyophilized form and when frozen in solution at −20° C. (40 and 80 µM).

TABLE 5

Osmium Mediator Labels

| Mediator Label | Concentration Response | Inhibition with Antibody | Reversal | Comments |
| --- | --- | --- | --- | --- |
| Os-SMCC-Alc | Linear | PAB IS (≦92%)<br>PAB DE (≦97%)<br>MAB (≦50%) | Yes with BSA-Alc polyhaptan | % = Inhibition values ranged from 16% to 97% depending on age of Os-SMCC stock solution. Degrades in solution. |
| Os-SATA-Alc | Linear | PAB IS (≦44%) | Yes with BSA-Alc polyhaptan | Stability similar to SMCC. |
| Os-DSG-Alc | Linear | PAB IS (≦91%)<br>PAB DE (≦87%)<br>MAB (≦78%) | Yes with BSA-Alc polyhaptan | More stable than conjugate made with SATA and SMCC crosslinker but still degrades in solution. |
| Os-SATA-A₀ | Linear | Yes with Sheep B<HbA₀> (≦84%).<br>No with Zymed rabbit antibodies | No with A₀HB-peptide#1 | A₀ conjugate was found to be unstable in solution. Conjugate was not lyophilized. |

Figure 6:
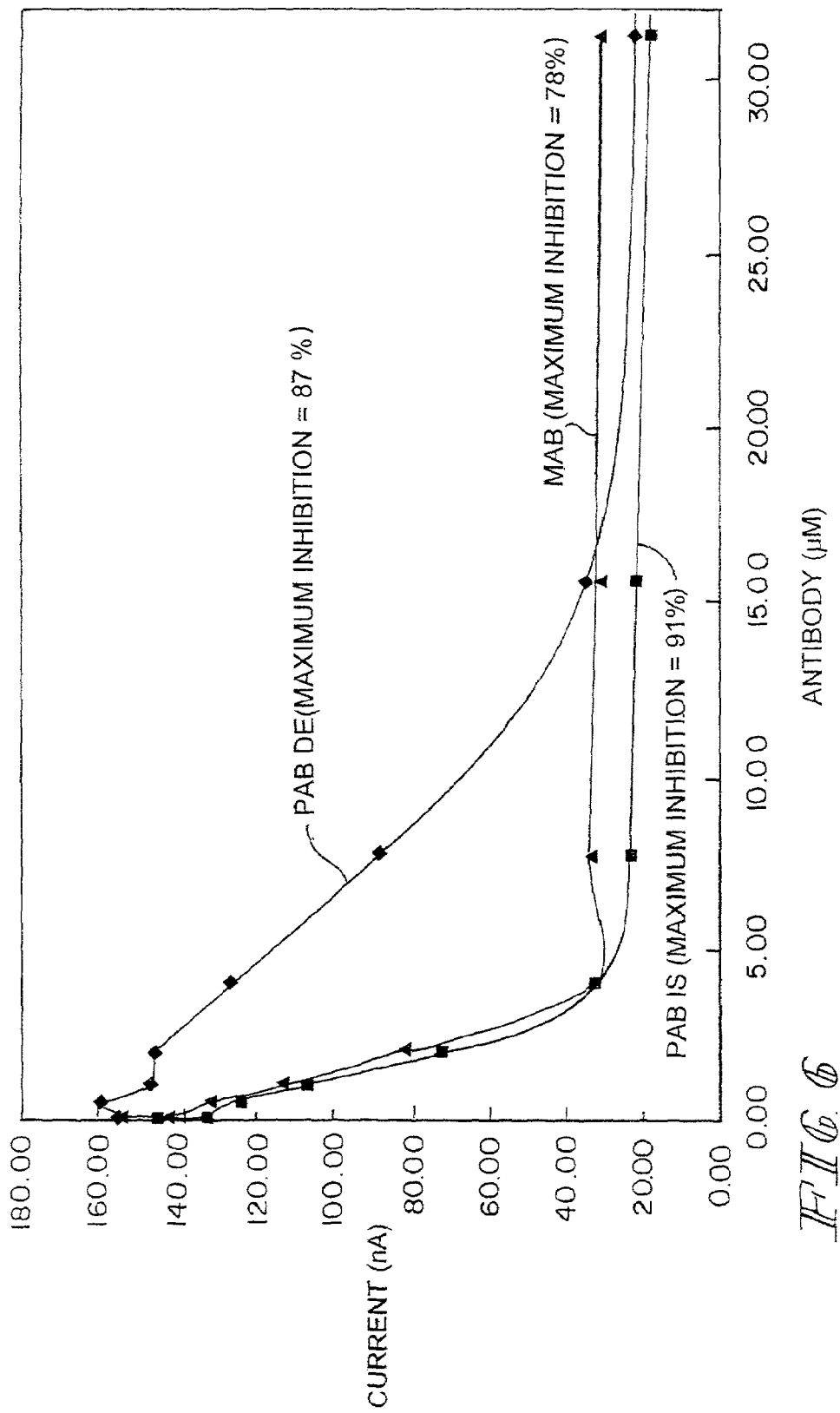
FIG. 6 is a graphic illustration of current flow vs. time using an interdigitated array electrode.
Figure 7:
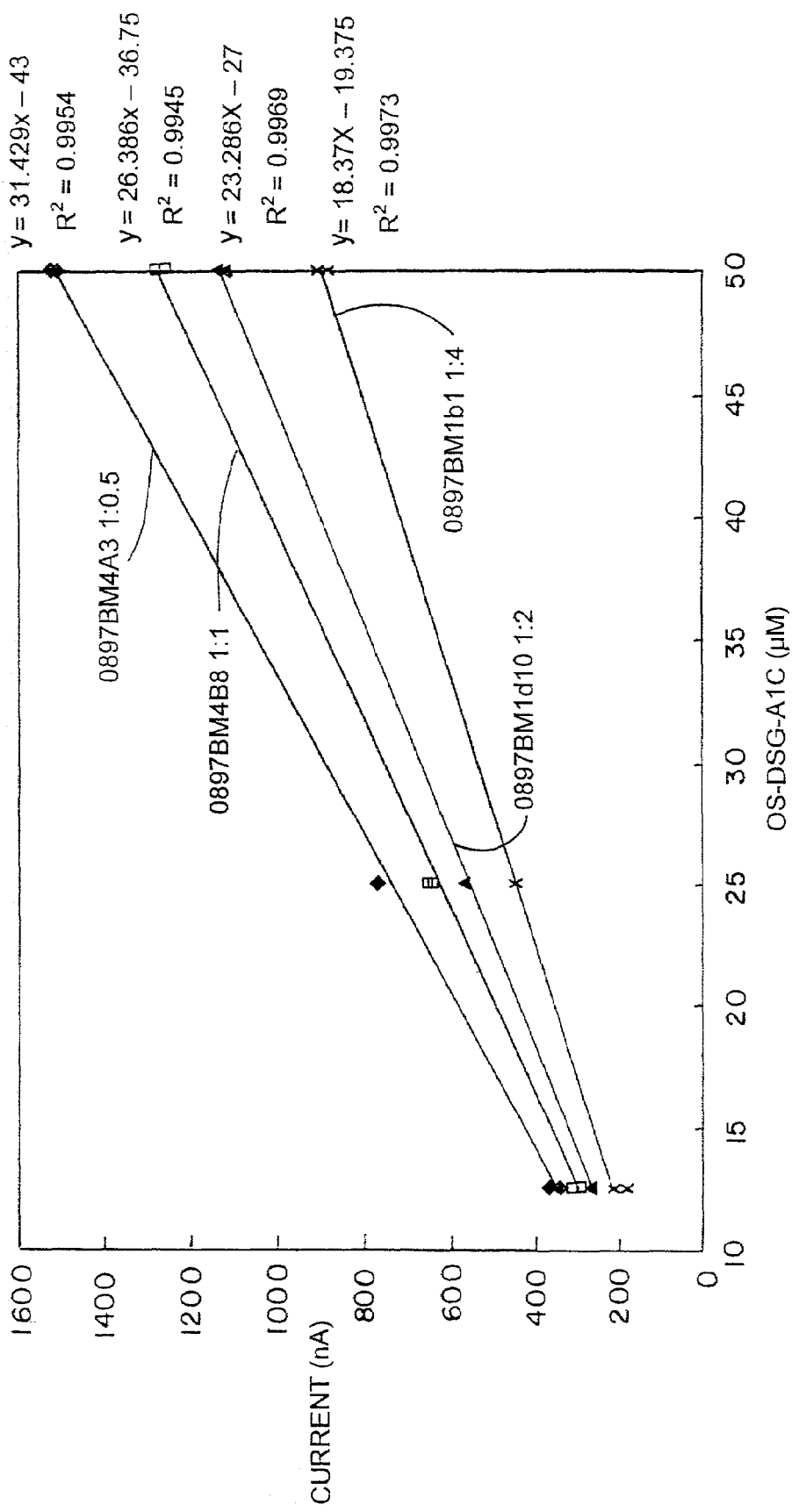
FIG. 7 is a graphic illustration of the effect of the dimensions of the interdigitated array electrode structure on current flow as a function of concentration of an osmium conjugate (Os-DSG-Alc).

Polyclonal DE (ion-exchange) purified sheep antibody is used in the TinaQuant HbA1c assay. IS (immunosorbent) antibody is prepared using standard IS purification methodology. Samples of a monoclonal antibody were also obtained for evaluation. Inhibition curves were performed in solution with all mixing occurring in microcentrifuge tubes. Assays were measured by applying 20 µL onto 6 mm² palladium electrodes with the conditions shown in Table 5. Inhibition curves with the three hemoglobin A1c antibodies (PAB IS, PAB DE, and MAB) were generated by fixing OS-DSG-A1c at 5 µM and varying the antibody concentration. Both PAB IS and MAB showed the expected stoichiometric relationship for inhibition with the osmium peptide conjugate indicating efficient and fast binding of the antibody to the A1c peptide. The polyclonal IS and monoclonal both showed steep inhibition curves with maximum change being reached close to 5 µM. Additional antibody above 5 µM showed little effect on increasing the inhibition. The less purified PAB DE antibody had a much smaller slope and as expected required more than 3 times the amount to get close to maximum inhibition. FIG. 6 shows the inhibition curves for each of the HbA1c antibodies tested. From the inhibition curves we were able to select reasonable concentrations of antibody for maximum reversal with A1c samples.

Inhibition curves were also performed for the Os-SMCC-A1c (Max=97%) and OS-SATA-A1c (Max=44%) mediator labels. Stability of the mediator labels were also evaluated by monitoring % inhibition values over time. All of the mediator labels showed some degradation when stored in dilute solutions (40 µM) at RT. Samples frozen at −20° C. appear to be stable.

Figure 10:
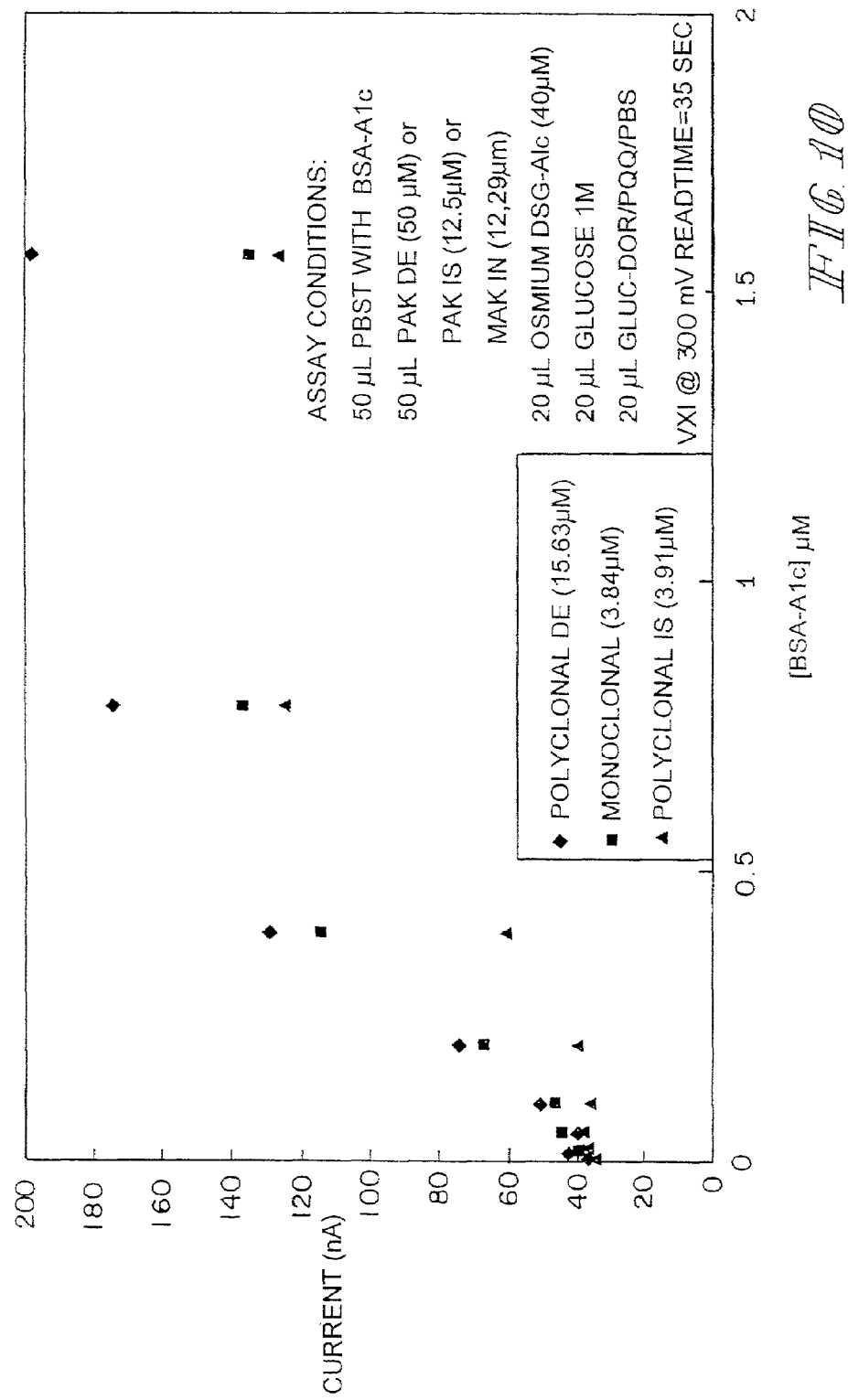
FIG. 10 is a graphic illustration of the effect of concentration of an unlabeled conjugate (BSA-Alc) on current flow in a solution containing osmium labeled conjugate (osmium-DSG-Alc)) in the presence of three separate Alc-recognizing antibody compositions.
Figure 11:
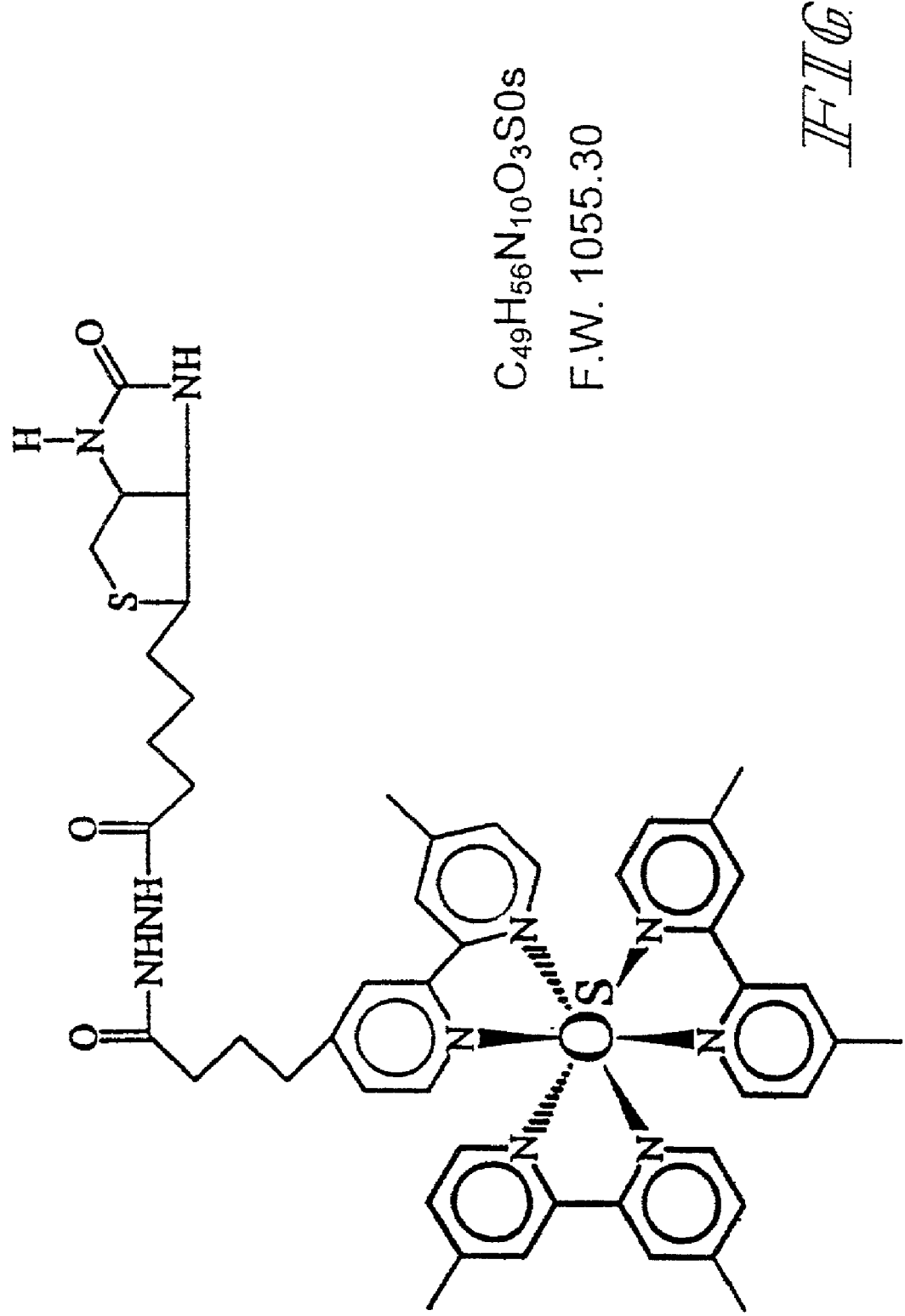
FIG. 11 illustrates the structure of a tris(bipyridyl) osmium labeled conjugate of this invention.
Figure 12:
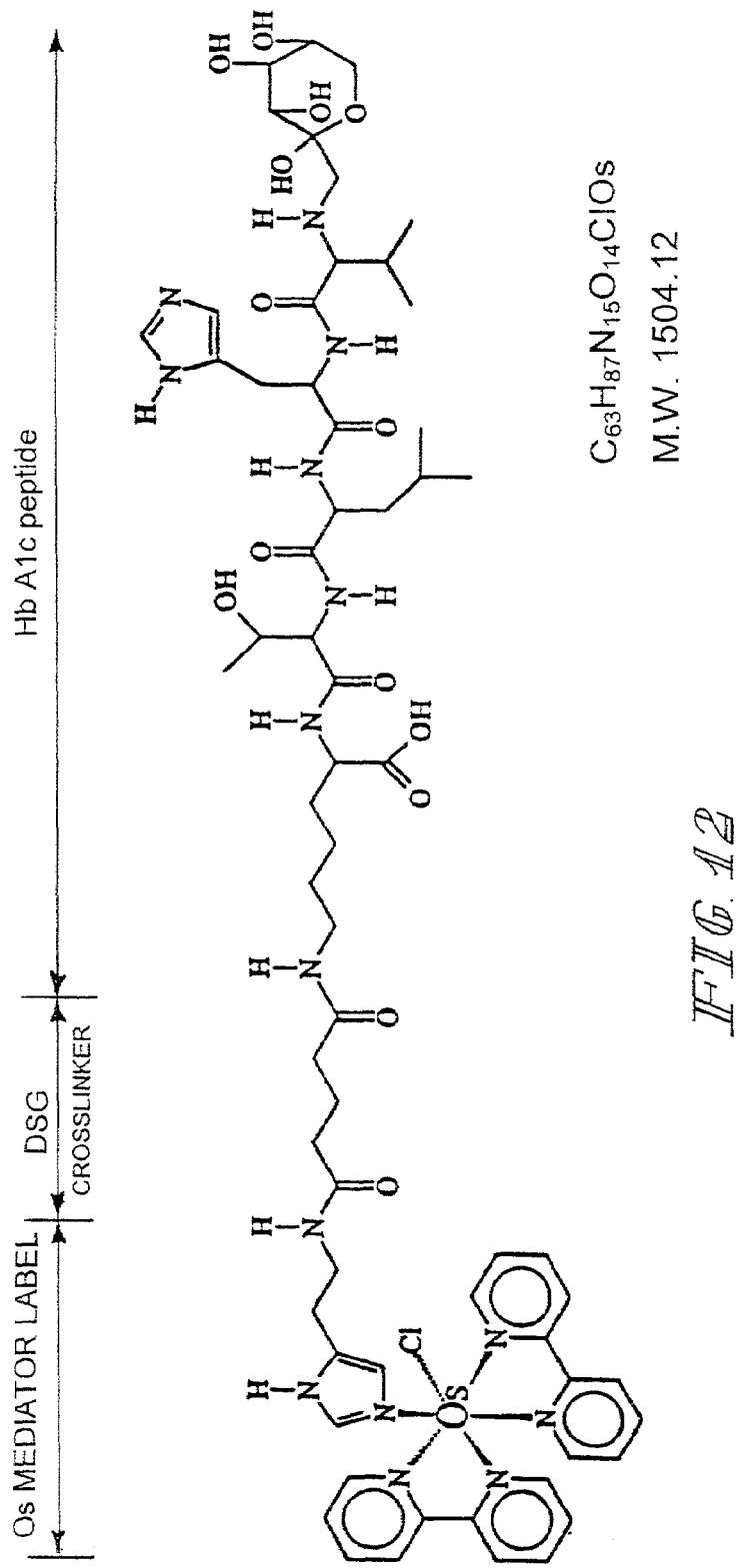
FIGS. 12–14 are similar and each depict the chemical structure of a bis(bipyridyl) imidazolyl chloroosmium labeled peptide conjugate.
Figure 13:
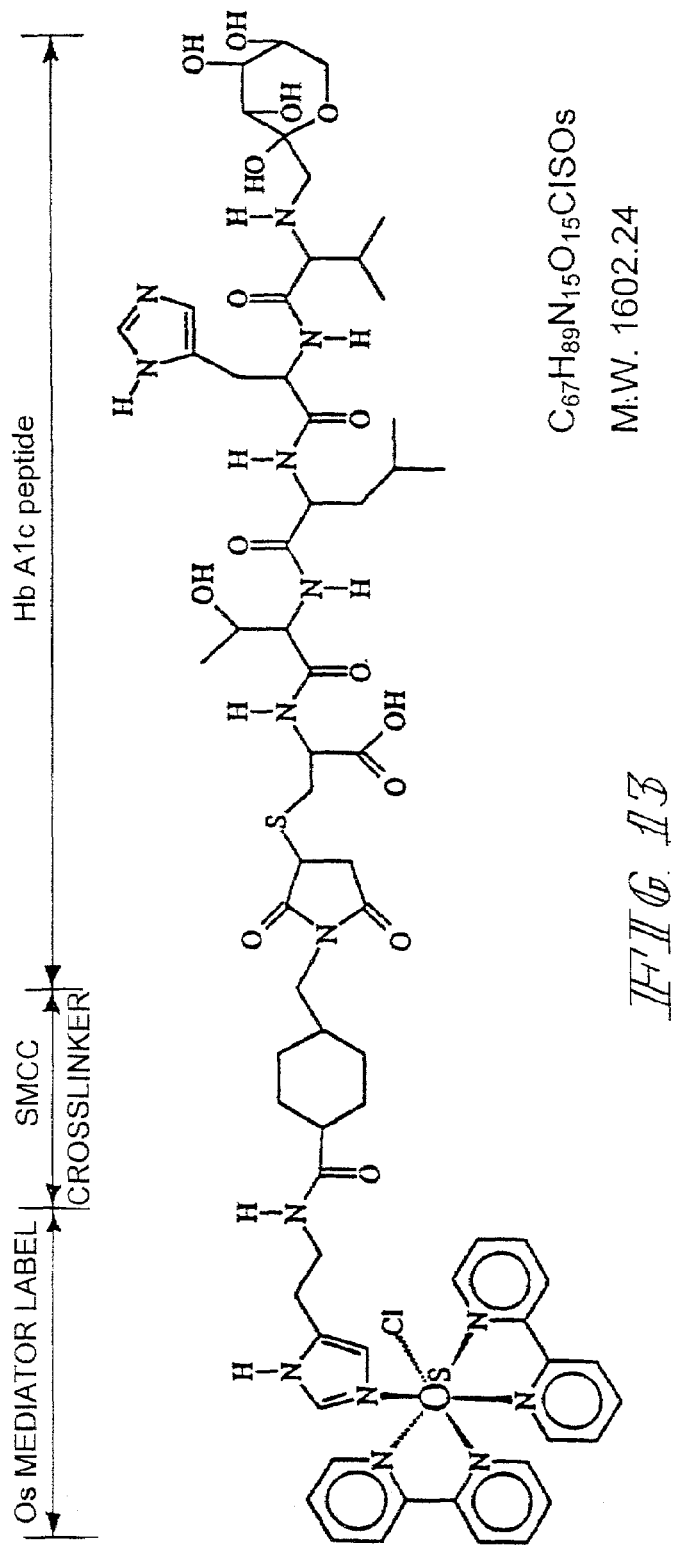
Figure 14:
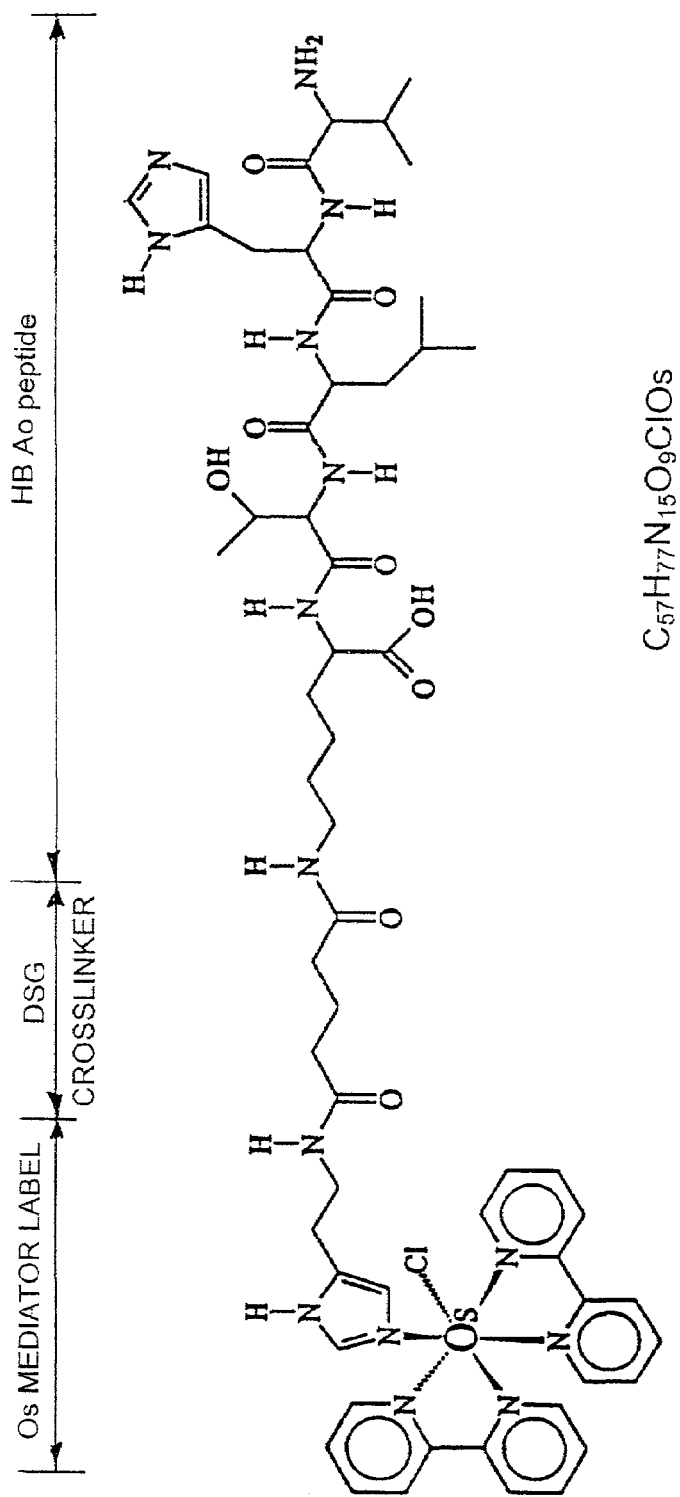

For demonstrating inhibition reversal, antibody concentrations of 4 µM for both PAB IS and MAB and 15 µM for PAB DE were chosen from the inhibition curves shown above. Reversal curves were then generated using a series of dilutions of BAS-A1c polyhaptan with a ~1:1 A1c:BSA. The BSA-A1c acts as our sample and binds to the antibody. FIG. 10 shows the reversal curves for the three antibodies.

While these feasibility studies for a HbA1c immunoassay used an enzyme mediated amplification method. (Glucdor/PQQ/glucose was used to regenerate reduced mediator after oxidation at the electrode surface providing a higher diffusion controlled current is given by the cottrell equation), they are considered to be indicative of results attainable with the use of IDA electrodes with bipotentiostatic control in accordance with this invention.

The invention claimed is:

1. A method for measuring the concentration of an analyte in a sample of a liquid, said method comprising contacting said sample with predetermined amounts of
   (1) a specific binding partner for said analyte, and
   (2) a detectable compound of the formula:

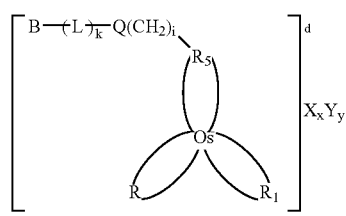

wherein

R and $R_1$ are the same or different and are 2,2'-bipyridyl, 4,4'-disubstituted-2,2'-bipyridyl, 5-5'-disubstituted,-2,2'-bipyridyl, 1,10-phenanthrolinyl, 4,7-disubstituted-1,10-phenanthrolinyl, or 5,6-disubstituted-1,10-phenanthrolinyl, wherein each substituent is a methyl, ethyl, or phenyl group, $R_5$ is 4-substituted-2,2'-bipyridyl or 4,4'-disubstituted-2,2'-bipyridyl wherein the 4-substituent is the group $B\text{-}(L)_k\text{-}Q(CH_2)_i\text{-}$ and the 4'-substituent is a methyl, ethyl or phenyl group;

R, $R_1$ and $R_5$ are coordinated to Os through their nitrogen atoms;

Q is O, S, or $NR_4$ wherein $R_4$ is hydrogen, methyl or ethyl;

—L— is a divalent linker;

k is 1 or 0;

i is 1, 2, 3, 4, 5 or 6;

B comprises a ligand that binds to the specific binding partner and is selected so that the detectable compound binds competitively with the analyte to said binding partner;

d is +2 or +3;

X and Y are anions selected from monovalent anions chloride, bromide, iodide, fluoride, tetrafluoroborate, perchlorate, and nitrate and divalent anions sulfate, carbonate or sulfite wherein x and y are independently 0, 1, 2, or 3 so that the net charge of $X_xY_y$ is −2 or −3; and determining electrochemically the concentration of the detectable compound not bound to the specific binding partner, wherein the concentration of the detectable compound not bound to the specific binding partner is proportional to the concentration of analyte present in the sample of fluid.

2. The method of claim 1 wherein the liquid sample is diluted blood, the analyte is glycosylated hemoglobin and the group B in the detectable compound comprises a glycosylated peptide of the formula Gluc-Val-His-Leu-Thr (SEQ. ID NO. 1).

3. The method of claim 2 further comprising the step of determining the concentration of total hemoglobin or unglycosylated hemoglobin in the liquid sample, and calculating the ratio of the concentration of glycosylated hemoglobin to unglycosylated hemoglobin.

4. The method of claim 1 wherein the concentration of the unbound detectable compound is determined by dc voltammetry using an interdigitated microarray electrode.

* * * * *